(12) United States Patent
Greenwood et al.

(10) Patent No.: US 6,183,735 B1
(45) Date of Patent: Feb. 6, 2001

(54) IMMORTALIZED RETINAL PIGMENTARY EPITHELIAL CELL LINES AND THEIR APPLICATIONS

(75) Inventors: John Greenwood, London; Peter Adamson, Croydon; Raymond Lund, London, all of (GB)

(73) Assignee: Neurotech, SA, Evry (FR)

( * ) Notice: Under 35 U.S.C. 154(b), the term of this patent shall be extended for 0 days.

(21) Appl. No.: 08/973,553

(22) PCT Filed: Apr. 18, 1997

(86) PCT No.: PCT/FR97/00709

§ 371 Date: Jan. 22, 1998

§ 102(e) Date: Jan. 22, 1998

(87) PCT Pub. No.: WO97/40139

PCT Pub. Date: Oct. 30, 1997

(30) Foreign Application Priority Data

Apr. 19, 1996 (FR) .................................................. 96 04964

(51) Int. Cl.[7] .......................... A61K 35/00; C12N 15/85; C12N 15/63; C07H 21/04
(52) U.S. Cl. .......................... 424/93.21; 424/93.2; 435/6; 435/320.1; 435/325; 435/353; 435/440; 536/23.1; 536/23.5; 536/23.7
(58) Field of Search .............................. 424/93.1, 93.21, 424/93.2; 435/6, 440, 325, 353, 320.1; 536/23.1, 23.7, 23.72, 23.5

(56) References Cited

PUBLICATIONS

Lloyd, A. DDT vol. 2, No. 10, pp. 397–398 (Oct. 1997).*
Kawasaki, Y. et al. Investigative Ophthalmology & Visual Science. 36(4): pS550 (Mar. 1995).*
Greenwood, J. et al. Journal of Neuroimmunology 71 (1996) pp. 51–63.*

Wang, Y.F. et al. Journal of Neuroimmunology 48 (Dec. 1993), pp. 161–168.*

Dutt, K. et al. Oncogene 5, (1990) pp. 195–200.*

Chou, J.Y. Molecular Endocrinology. 3, (Oct. 1989), pp. 1511–1514.*

Federiksen, K. et al. Neuron. 1, (Aug. 1988), pp. 439–448.*

* cited by examiner

*Primary Examiner*—John S. Brusca
*Assistant Examiner*—Mark L. Shibuya
(74) *Attorney, Agent, or Firm*—Mintz, Levin, Cohn, Ferris, Glovsky and Popeo, P. C.; Ivor R. Elrifi; John T. Prince

(57) ABSTRACT

The invention features immortalized retina-derived (retinal endothelial or retinal epithelial pigmentary) cell lines capable of being implanted in the retina and of carrying a therapeutic substance to the eye and to the central nervous system. Such lines can also be used as a model for studying blood central nervous system interfaces. These lines are derived from primary retinal cultures selected from the group consisting of primary retinal endothelial cells and primary retinal epithelial cells, comprise a nucleic acid fragment containing at least one immortalizing fragment of a heat-sensitive viral oncogene, which nucleic fragment is optionally associated with at least one selection gene, and have the morphological characteristics and at least the expression characteristics of the surface antigens of corresponding primary cultures.

13 Claims, 22 Drawing Sheets

WO 97/40139             No de la demande internationale: PCT/FR97/00709

| MICRO-ORGANISMES |
|---|
| Feuille facultative relative au micro-organisme mentionné au page 4 ligne 15 de la description |

A. IDENTIFICATION DU DÉPÔT

Collection Nationale de Cultures de Micro-organismes

Adresse de l'institution de dépôt (y compris le code postal et le pays)

28 rue du Docteur Roux, 75724 PARIS CEDEX 15

| Date du dépôt    18 avril 1996 | N° d'ordre     I-1694 |
|---|---|

B. INDICATIONS SUPPLÉMENTAIRES (à ne remplir que si nécessaire). Une feuille séparée est jointe pour la suite de ces renseignements ☐

"En ce qui concerne les désignations dans lesquelles un brevet européen est demandé, un échantillon du micro-organisme déposé ne ser accessible, jusqu'à la publication de la mention de la délivrance du brevet européen ou jusqu'à la date à laquelle la demande sera rejetée, retirée ou réputée retiré, que par la remise d'un échantillon à un expert désigné par le requérant. (règle 28.4) de la CBE)".

C. ÉTATS DÉSIGNÉS POUR LESQUELS LES INDICATIONS SONT DONNÉES (si les indications ne sont pas données pour tous les États désignés)

EUROPE                 NOUVELLE-ZELANDE
    AUSTRALIE            ETATS-UNIS D'AMERIQUE
    CANADA
    JAPON

D. INDICATIONS FOURNIES SÉPARÉMENT (à ne remplir que si nécessaire)

Les indications énumérées ci-après seront soumises ultérieurement au Bureau international (spécifier la nature générale des indications p. ez., "No d'ordre du dépôt")

E. ☐ La présente feuille à été reçue avec la demande internationale lorsque celle-ci a été déposée (à vérifier par l'office récepteur)

(Fonctionnaire autorisé)

☐ Date de réception (en provenance du déposant) par le Bureau International

C. BEDNARICK (Fonctionnaire autorisé)

Formulaire PCT/RO/134 (Janvier 1981)

Fig. 18

WO 97/40139  No de la demande internationale: PCT/FR97/00709

| MICRO-ORGANISMES | |
|---|---|
| Feuille facultative relative au micro-organisme mentionné au page 4 ligne 11 de la description | |

A. IDENTIFICATION DU DÉPÔT

Collection Nationale de Cultures de Micro-organismes

Adresse de l'institution de dépôt (y compris le code postal et le pays)

28 rue du Docteur Roux, 75724 PARIS CEDEX 15

| Date du dépôt | 18 avril 1996 | N° d'ordre | I-1695 |
|---|---|---|---|

B. INDICATIONS SUPPLÉMENTAIRES (à ne remplir que si nécessaire). Une feuille séparée est jointe pour la suite de ces renseignements ☐

"En ce qui concerne les désignations dans lesquelles un brevet européen est demandé, un échantillon du micro-organisme déposé ne ser accessible, jusqu'à la publication de la mention de la délivrance du brevet européen ou jusqu'à la date à laquelle la demande sera rejetée, retirée ou réputée retiré, que par la remise d'un échantillon à un expert désigné par le requérant. (règle 28.4) de la CBE)".

C. ÉTATS DÉSIGNÉS POUR LESQUELS LES INDICATIONS SONT DONNÉES (si les indications ne sont pas données pour tous les États désignés)

| EUROPE | NOUVELLE-ZELANDE |
|---|---|
| AUSTRALIE | ETATS-UNIS D'AMERIQUE |
| CANADA | |
| JAPON | |

D. INDICATIONS FOURNIES SÉPARÉMENT (à ne remplir que si nécessaire)

Les indications énumérées ci-après seront soumises ultérieurement au Bureau international (spécifier la nature générale des indications p. ez., "No d'ordre du dépôt")

E. ☐ La présente feuille à été reçue avec la demande internationale lorsque celle-ci a été déposée (à vérifier par l'office récepteur)

(Fonctionnaire autorisé)

☐ Date de réception (en provenance du déposant) par le Bureau International

C. BEDNARICK (Fonctionnaire autorisé)

Formulaire PCT/RO/134 (Janvier 1981)

Fig. 19

IMMORTALIZED RETINAL PIGMENTARY EPITHELIAL CELL LINES AND THEIR APPLICATIONS

This application claims priority under 35 U.S.C. 119(a) to French Patent Application 96 04964, filed Apr. 19, 1996.

BACKGROUND OF THE INVENTION

1. Field of the Invention

The present invention relates to novel immortalized cell lines of retinal origin (retinal endothelial and retinal pigmentary epithelial origin) which are capable of being implanted in the retina and of conveying a substance of therapeutic interest into the eye and the central nervous system. Such lines can also serve as a model for studying the blood/central nervous system interfaces.

2. Description of the Background

Both the blood-brain barrier and the blood-retina barrier are important in controlling the passage of substances to and from the neural parenchyma, especially in the maintenance of haemostasis.

In the retina, the blood-retina barrier comprises two different types of cells which are anatomically separate. The retinal vascular endothelium, which supplies the anterior portion of the retina, is currently considered to have an identical structure to the cerebral endothelium (Towler et al., J. Physiol., 1994, 480, 10-11P), whereas the cells of the retinal pigmentary epithelium cover the permeable vessels of the choroidal circulation and form the posterior barrier by means of their tight apical junctions; they are consequently similar to the tight junction epithelial cells of the choroid plexus.

The cerebral and retinal endothelia are of a different nature to the peripheral endothelium and do not serve only to express tight junctions and form a physical barrier. Other properties of the endothelium contribute to the specialized nature of this barrier, particular properties being the distribution and expression of substances such as the glucose transporter (GLUT-1), the transferrin receptor and P-glycoprotein (Pgp), the expression product of the drug resistance gene.

The cerebral and retinal endothelia also differ from the peripheral endothelium in their permeability to the circulating leukocytes.

The in vitro study of the molecular mechanisms of the induction of the endothelial phenotype has the disadvantage of being dependent on the availability, in primary cell cultures, of endothelial cells of cerebral or retinal vessels or pigmentary epithelial cells of the retina.

As far as in vivo transfer is concerned, the use of primary nerve tissues of foetal origin for cellular transplantation in human therapy gives rise to numerous ethical and practical problems; one alternative to this problem is to use primary cell lines of neural origin (for example neurons, glial cells, astrocytes) or non-neural cell cell lines (for example fibroblasts, myoblasts, chromaffin cells of the adrenal medulla, hepatocytes). Although the cell lines of the adrenal medulla, fibroblasts or myoblasts can actually release active substances in vivo, they are not normally present in the central nervous system, but can modify the normal function of the nervous system and cause a rejection reaction.

Because of the heterogeneity of the endothelial cells of different tissues, influenced by the environment of these cells, it was important to be able to have cells adapted to the retinal environment in order to have tools permitting a good morphological and physiological integration of the cells when they are implanted or grafted.

Consequently, the Inventors set themselves the task of providing immortalized cell lines derived from primary cultures of the endothelium of the blood-retina barrier and the retinal pigmentary epithelium of mammals, especially rodents and more particularly rats, which cell lines are better capable of meeting practical needs, especially in that all the lines obtained are stable and have most of the characteristics of the differentiated cells.

SUMMARY OF THE INVENTION

The present invention relates to immortalized mammalian cell lines, characterized in that they are derived from primary cultures of retinal cells selected from the group comprising the primary retinal endothelial cells and the primary retinal epithelial cells, in that they comprise a nucleic acid fragment containing at least one immortalizing fragment of a heat-sensitive viral oncogene, which nucleic acid fragment may be associated with at least one selection gene, and in that they stably exhibit the morphological characteristics and at least the surface antigen expression characteristics of the corresponding primary culture cells.

DETAILED DESCRIPTION OF THE INVENTION

Stability is understood as meaning the maintenance of the morphological and phenotypic characteristics of the immortalized lines for up to at least 30 passages and even up to more than 50 passages.

In one advantageous embodiment of said lines, they are derived from retinal endothelial cells and exhibit at least the morphological characteristics and antigen expression characteristics of the primary culture retinal endothelial cells, namely fusiform morphology, expression of the endothelial tissue markers such as RECA-1, constitutive expression of markers specific for the CNS endothelium, such as at least P-glycoprotein, GLUT-1 and the transferrin receptor, and absence of expression of surface antigens specific for the cerebral endothelial cells, such as the 1A8B antigen.

In another advantageous embodiment of said lines, they are derived from retinal pigmentary epithelial cells and exhibit the morphological characteristics and antigen expression characteristics of the primary culture retinal pigmentary epithelial cells, namely pavement morphology and expression of RET-PE2 and cytokeratins.

Surprisingly, such cells do not differ in their expression of the characteristics of the differentiated retinal endothelial cells or the differentiated retinal pigmentary epithelial cells.

Moreover:
- the retinal pigmentary epithelial cells are capable, in vivo, of integrating appropriately into the cytoarchitecture of the retina of a host mammal without proliferating, and of preventing the loss of photoreceptors, especially in rats of the RCS (Royal College of Surgeons) strain, and
- the retinal endothelial cells are capable, in vitro, of serving as a model for the blood-retina barrier in the absence or presence of the retinal pigmentary epithelial cells.

In another advantageous embodiment of said lines, the nucleic acid fragment containing at least one immortalizing fragment of an oncogene contains a fragment of a heat-sensitive SV40 T-oncogene.

This gave:
immortalized retinal endothelial cells, called IO/JG2/1, which were fusiform like the primary culture cells and expressed the above-mentioned markers specific for the CNS endothelial cells, as well as the same surface antigens and the same antigens of the major histocompatibility complex as the primary culture retinal endothelial cells, and immortalized retinal pigmentary epithelial cells, called IO/LD7/4, which were very similar to the primary culture cells; although not pigmented, these cells express the specific RET-PE2 antigen and the cytokeratins.

According to the invention, the immortalized retinal endothelial cells called IO/JG2/1 were deposited under no. I-1695 on Apr. 18th 1996 in the Collection Nationale de Cultures de Micro-organismes held by the Institut Pasteur, 28 rue de Docteur Roux, 75724 PARIS CEDEX 15.

According to the invention, the immortalized retinal pigmentary epithelial cells called IO/LD7/4 were deposited under no. I-1694 on Apr. 18th 1996 in the Collection Nationale de Cultures de Micro-organismes held by the Institut Pasteur.

The present invention further relates to cell lines derived from the immortalized lines as defined above, hereafter called vector cell lines, characterized in that they comprise at least one cell line as defined above, associated with an expression vector comprising a sequence coding for a polypeptide, a protein or a viral vector, optionally associated with at least one selection gene and optionally at least one marker gene, and in that they are capable, in vivo, of integrating into the retina and especially the subretinal space of a host mammal, preventing the loss of photoreceptors and producing said peptide, said protein or said viral vector.

In terms of the present invention, expression vector is understood as meaning any nucleic acid fragment integrated into the genome or present in the cytoplasm of said cell lines and capable of permitting the expression of said polypeptides, protein or viral vector.

All the lines according to the present invention (cell lines and vector lines) have the advantage of constituting a pure, homogeneous and sufficient source of cells of retinal origin for the purpose of reproducible application to transplantations, especially because all these lines have the phenotype of the primary culture lines.

As regards the vector lines more particularly, they integrate well into the retinal vascularization, are very well tolerated, release in vivo, over a long period, the active substance which they express, and can be used in the preparation of a composition for the treatment of primary or secondary ophthalmological or neurological disorders.

The present invention further relates to a model for studying and identifying the biochemical and cellular systems of the blood-retina barrier, characterized in that it comprises at least one cell line as defined above.

Apart from the foregoing provisions, the invention also comprises other provisions, which will become apparent from the following description referring to Examples of how to carry out the process forming the subject of the present invention, and to the attached drawings, in which:

FIGS. 1C–1F show the morphology of the primary cultures of retinal endothelial cells (1A), retinal pigmentary epithelial cells (1C) and the IO/JG2/1 immortalized clones (1B) and IO/LD7/4 immortalized clones (1D) according to the invention;

FIGS. 2A–C show transmission electron micrographs of the IO/LD7/4 cells (2A) and IO/JG2/1 cells (2B, 2C);

Figure 7A:
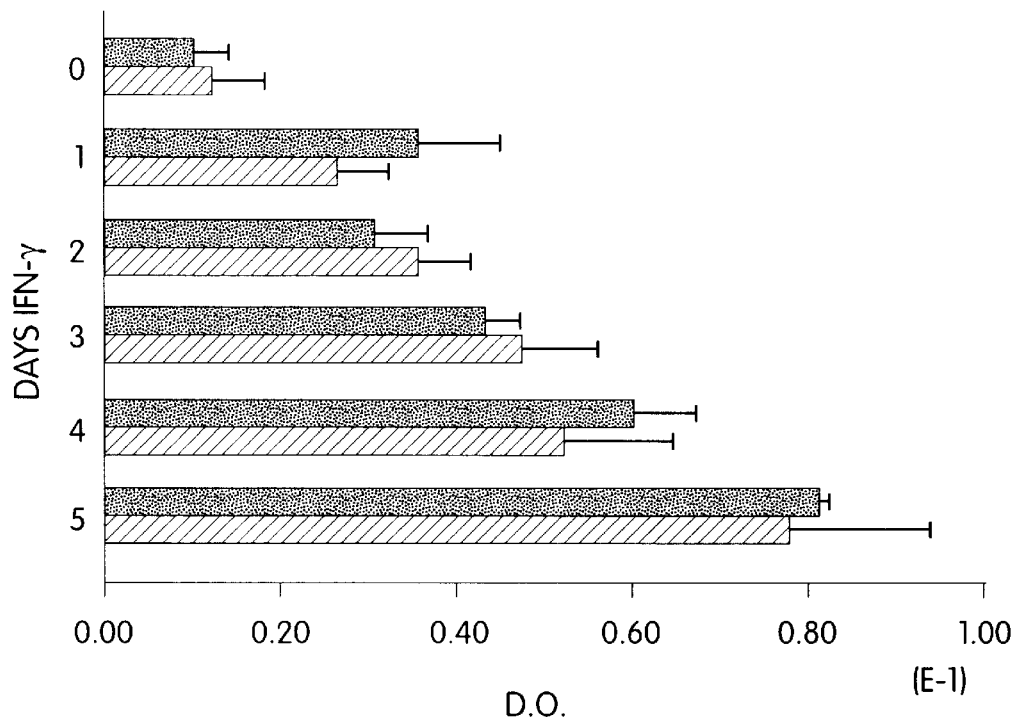
Figure 7B:
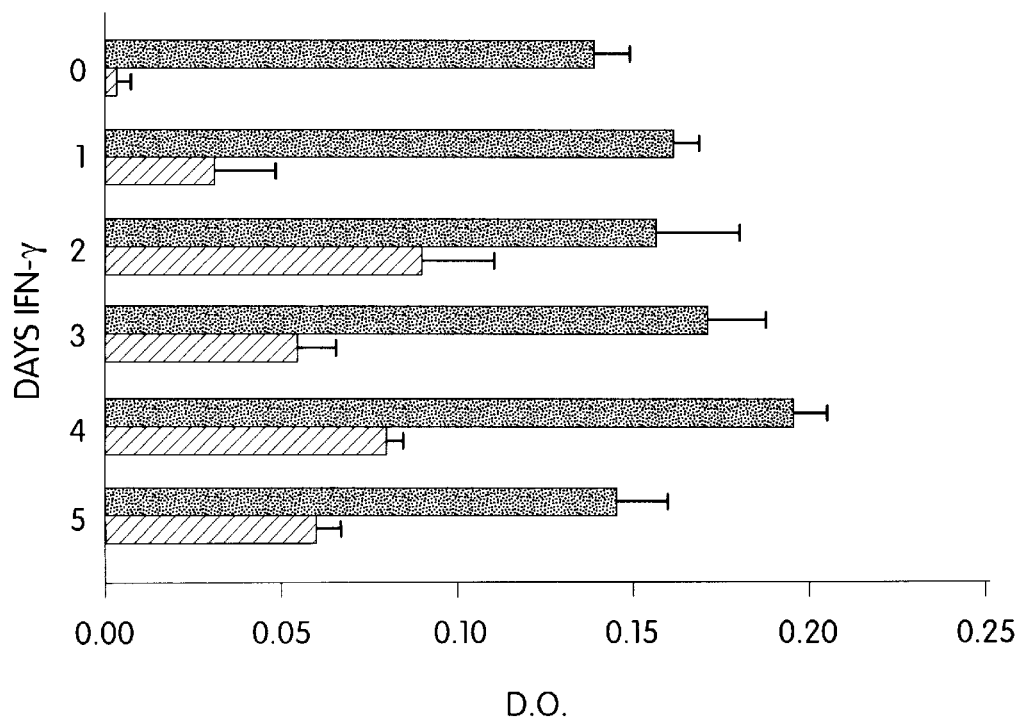
Figure 8:
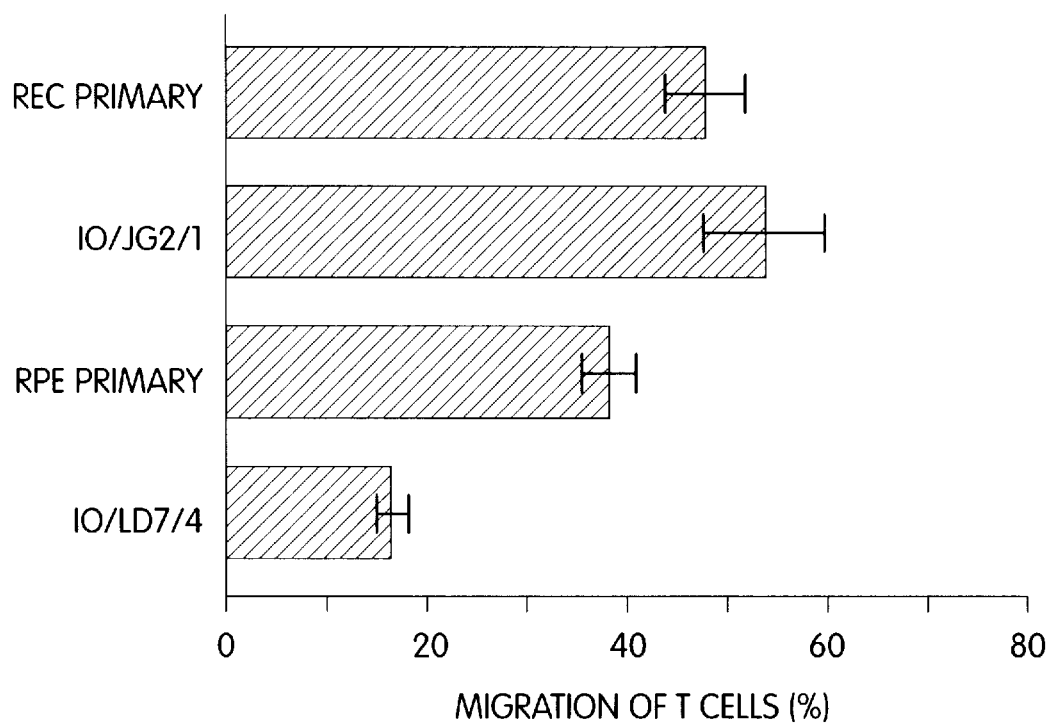
Figure 9:
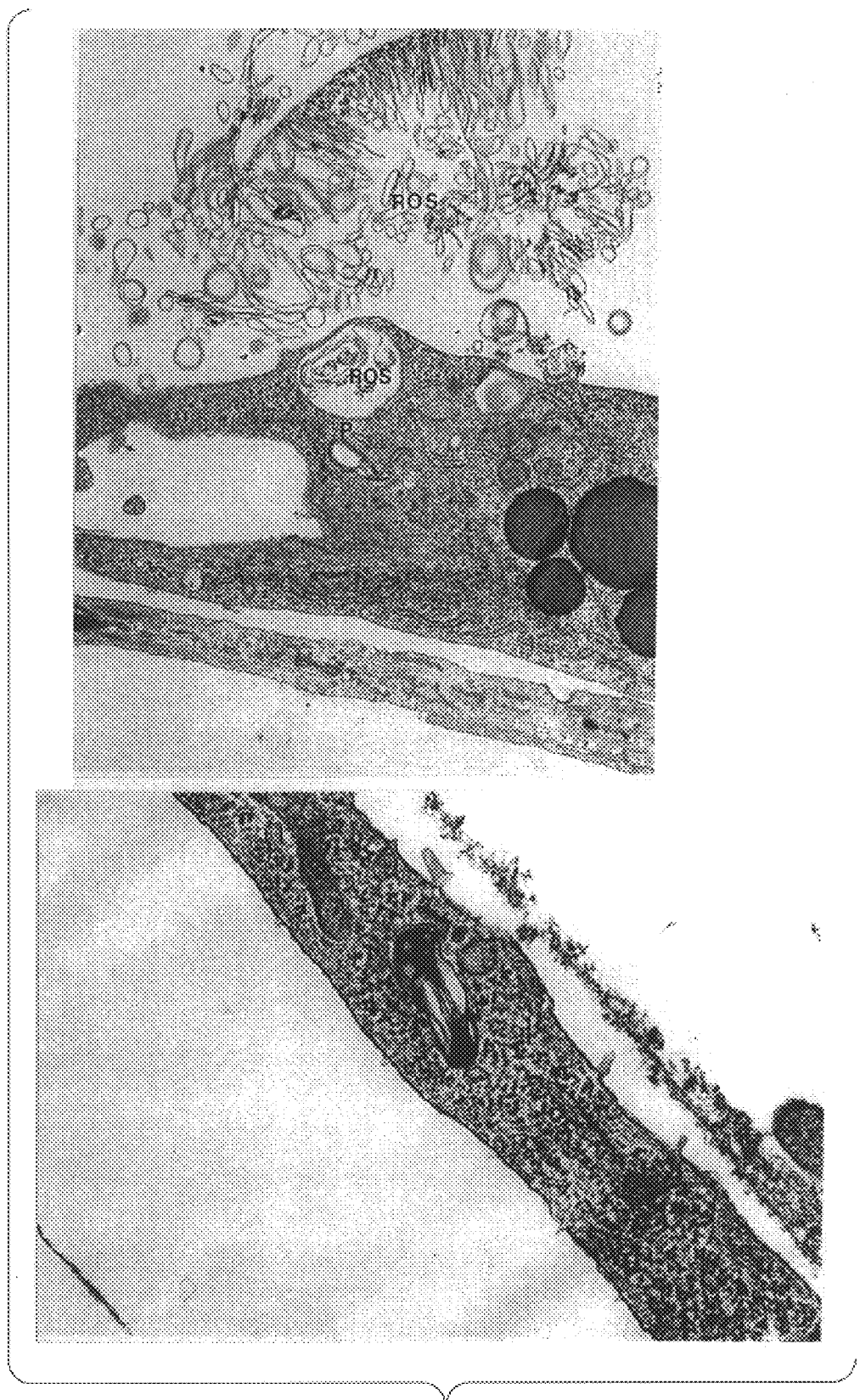
Figure 10:
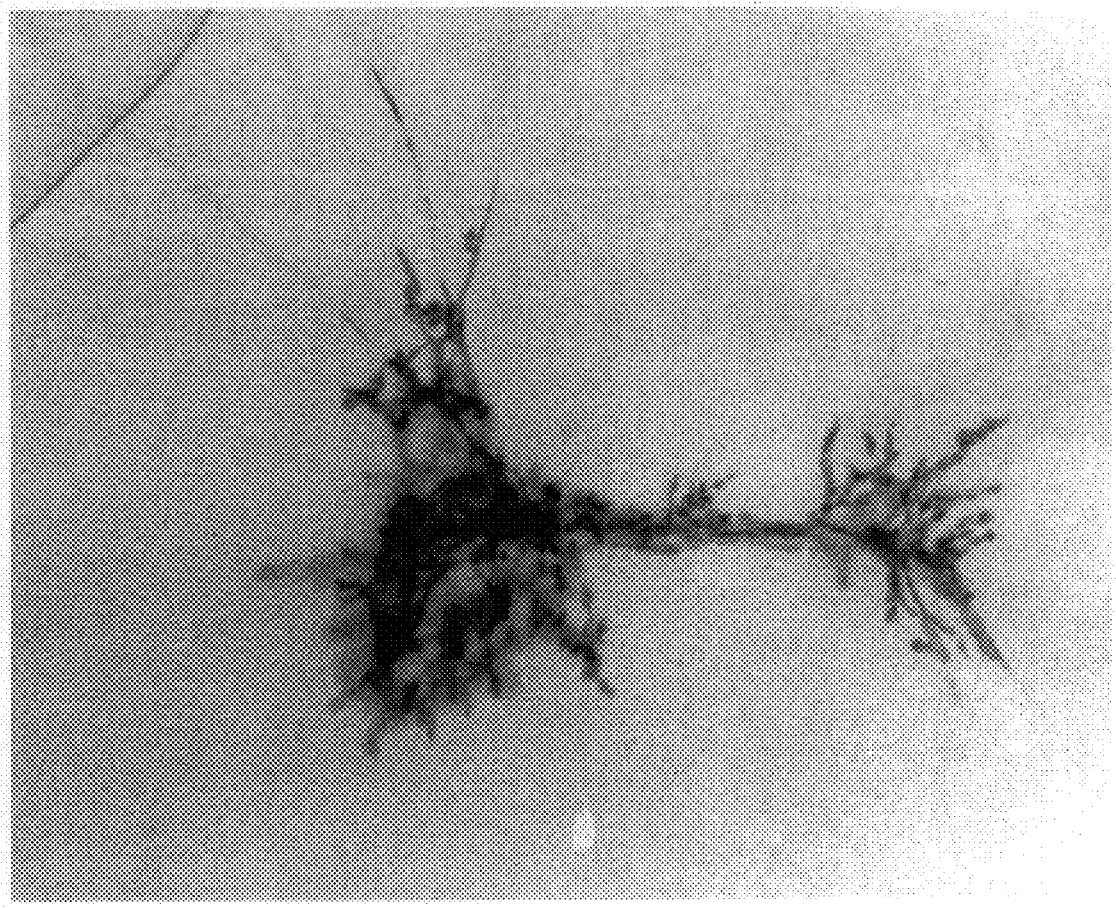
Figure 11:
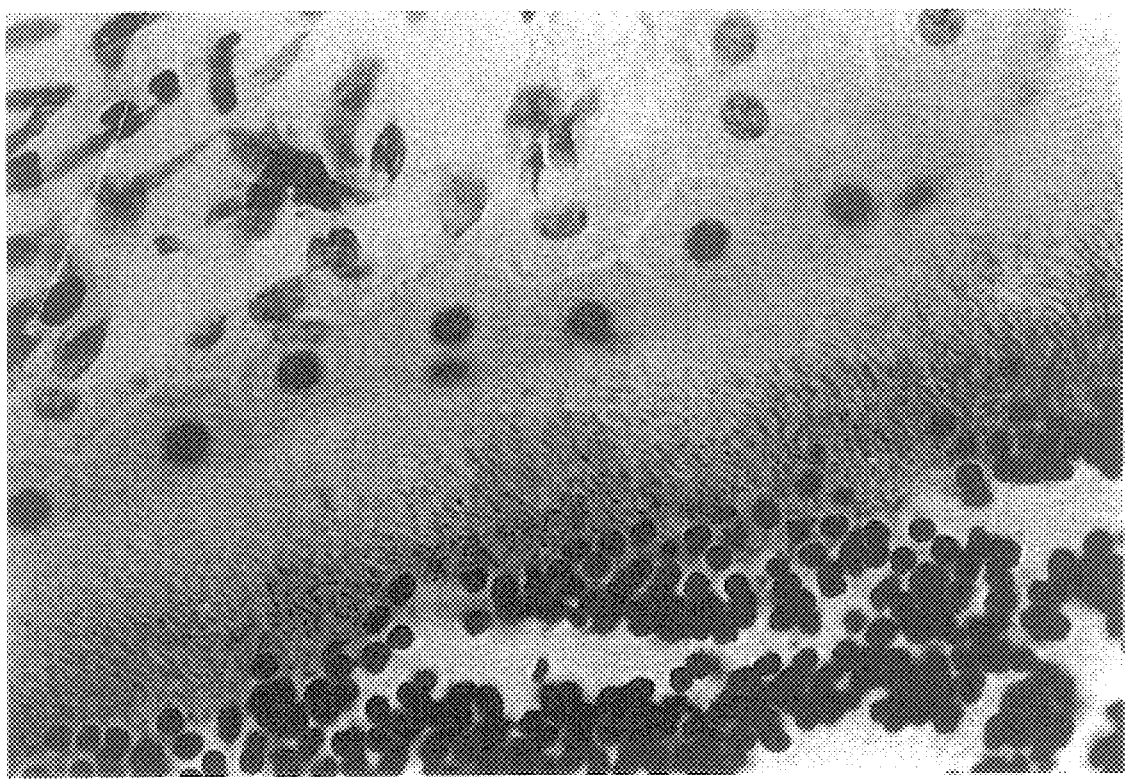
Figure 12A:
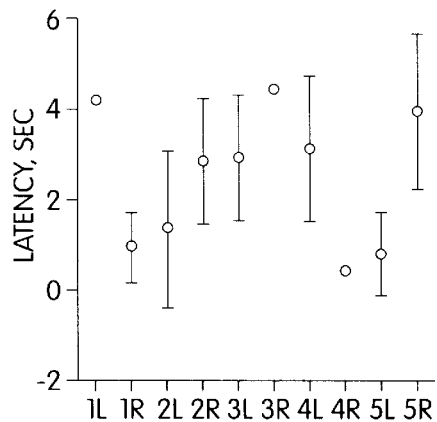
Figure 12B:
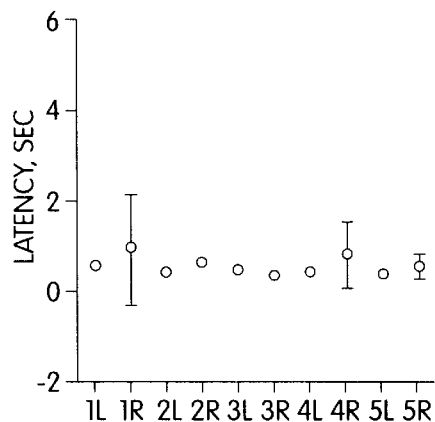
Figure 12C:
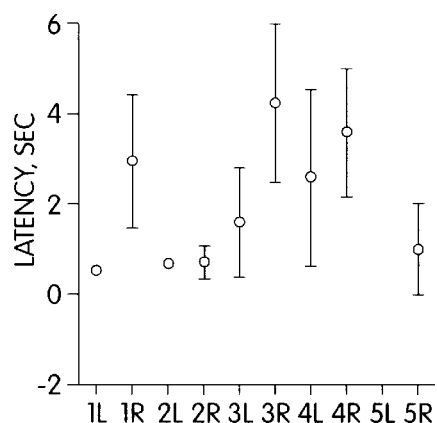
Figure 12D:
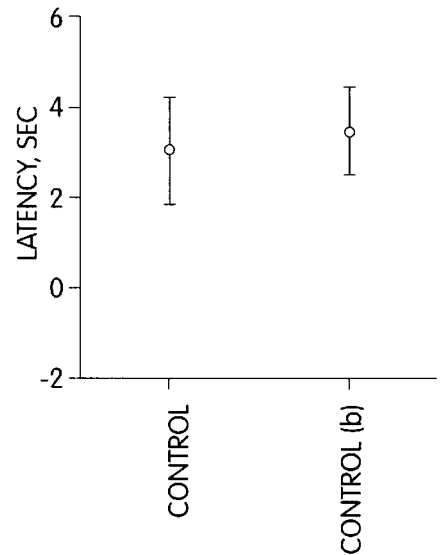
Figure 13A:
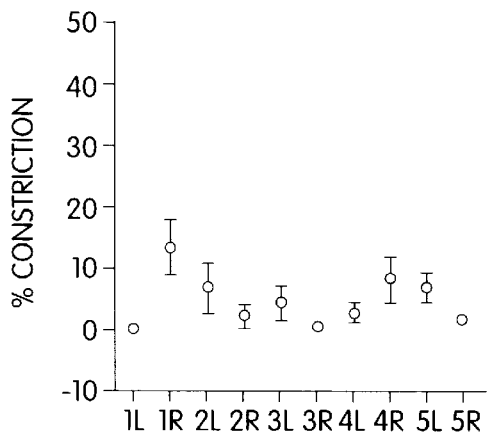
Figure 13B:
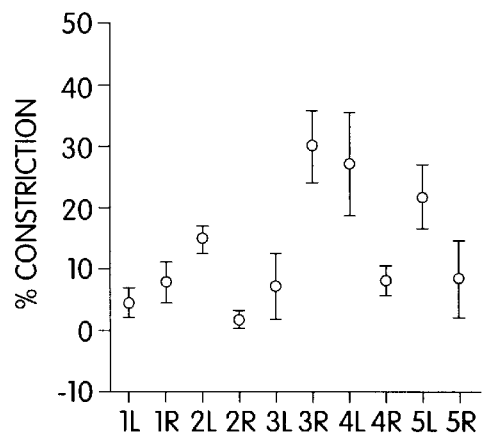
Figure 13C:
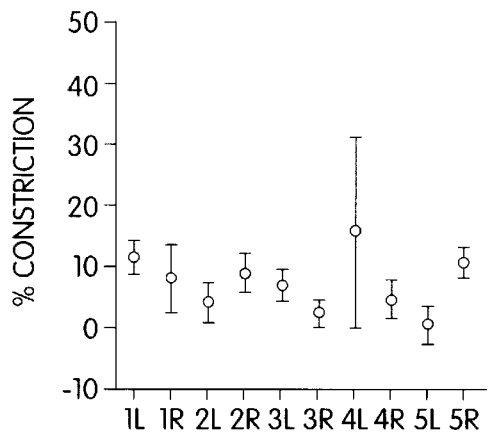
Figure 13D:
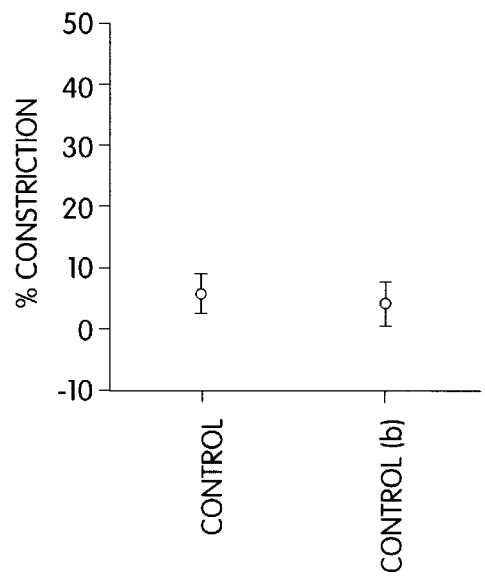
Figure 14:
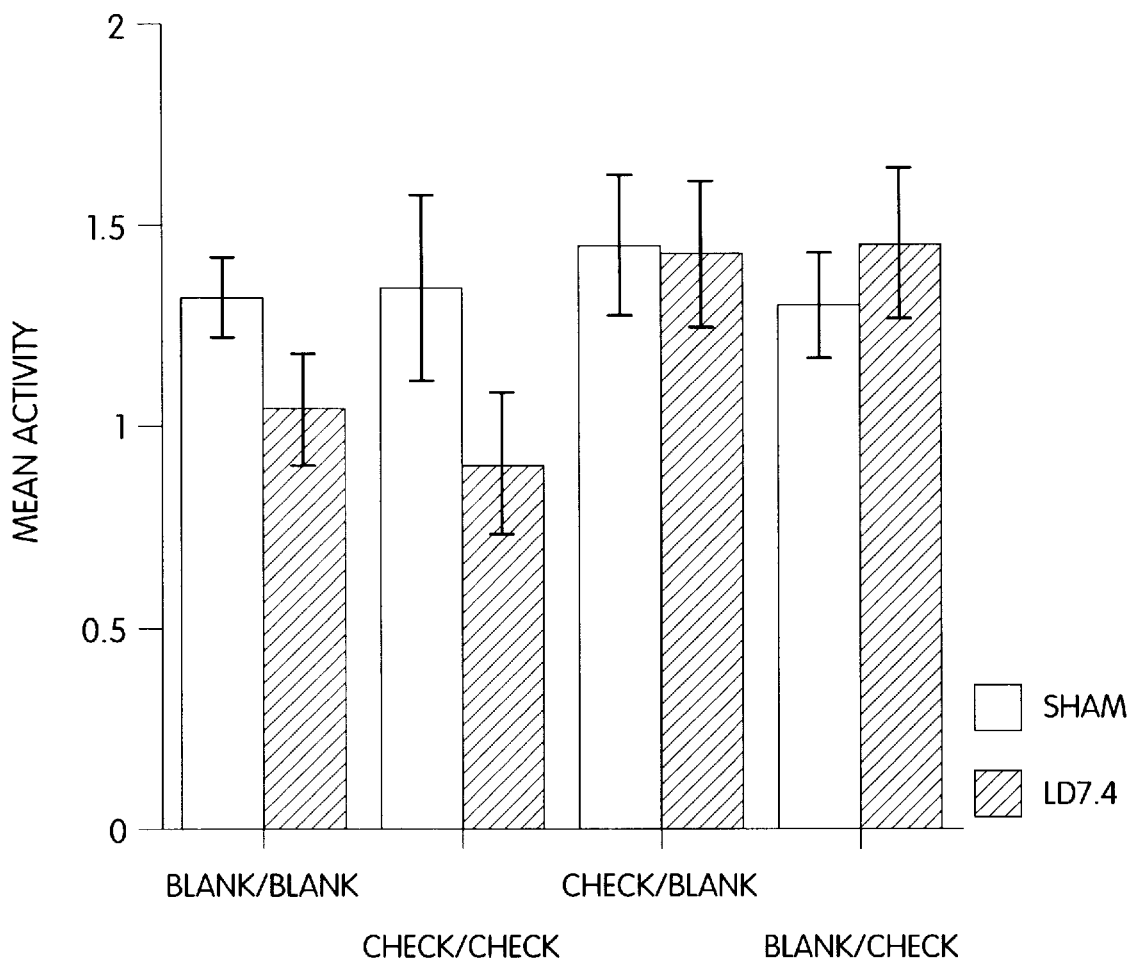
Figure 15:
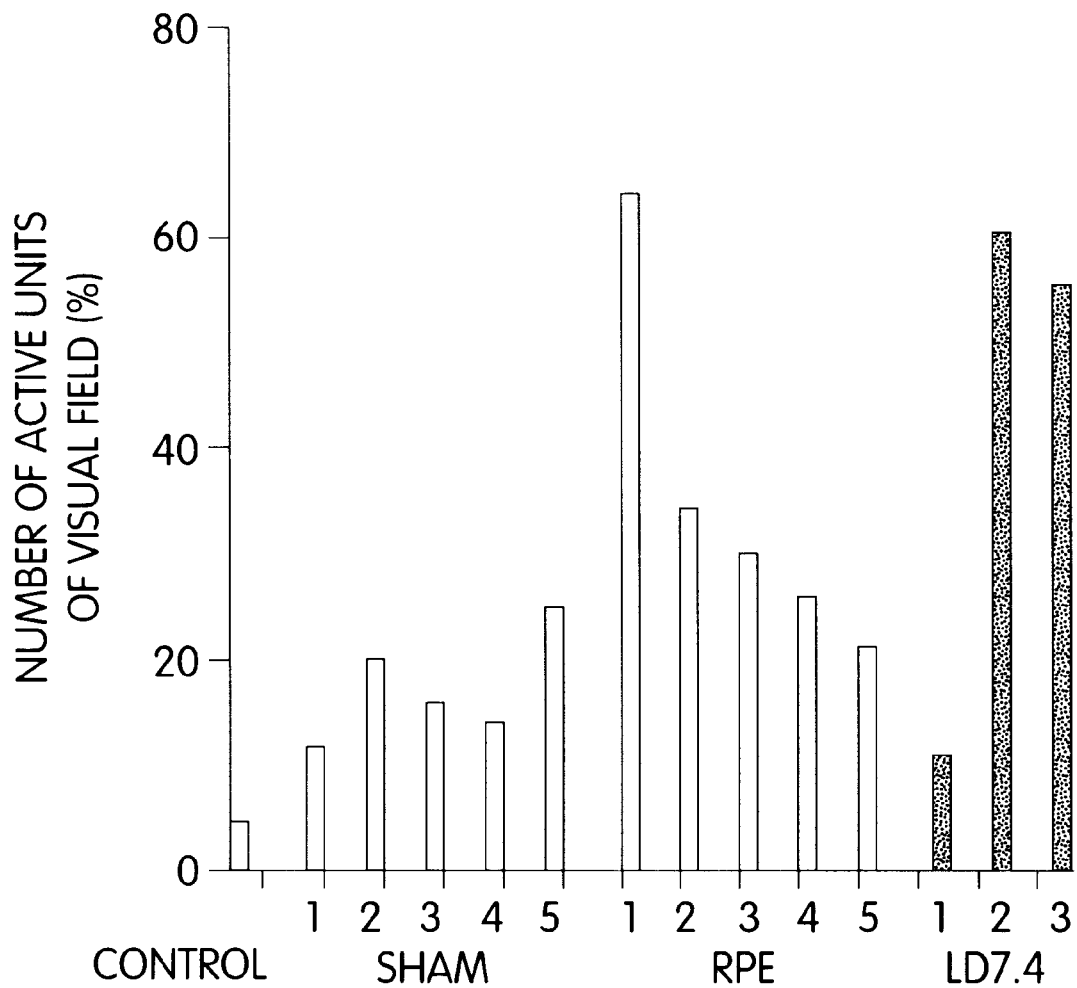
Figure 16:
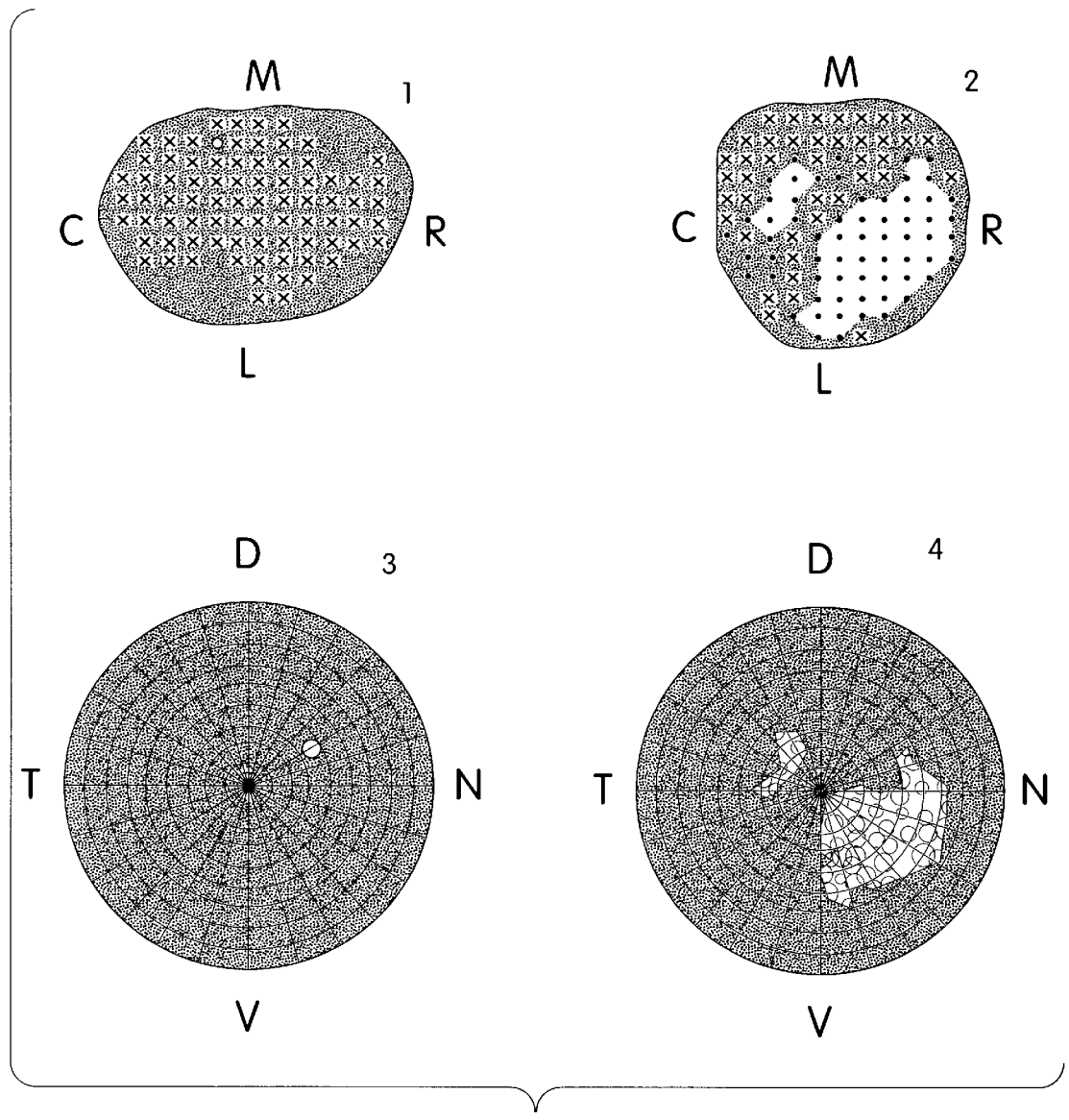
Figure 17A:
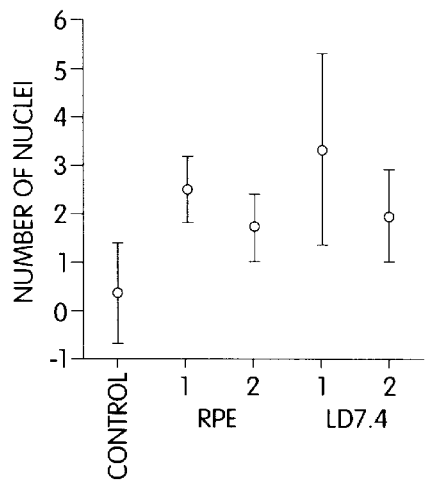
Figure 17B:
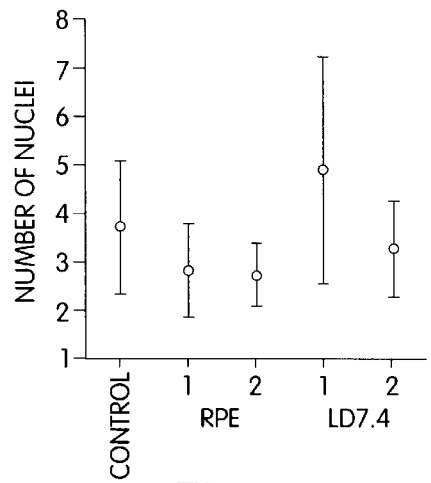
Figure 17C:
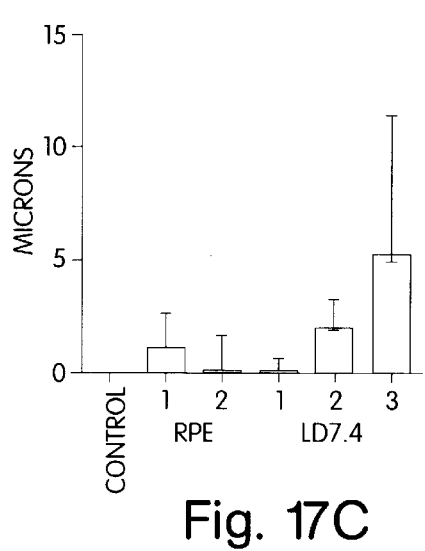
Figure 17D:
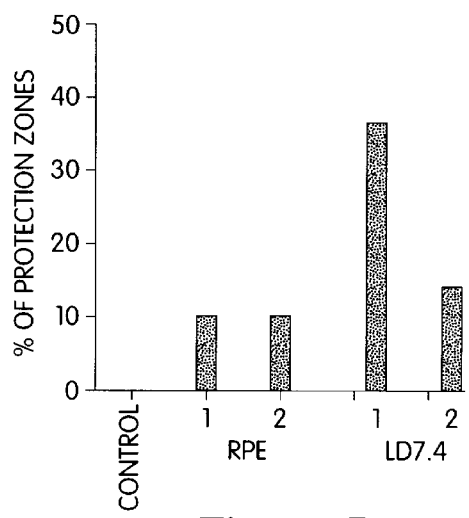

FIGS. 6A–6F show the expression of the adhesion molecule ICAM-1 (6A, 6B) and the antigens of the class I (6C, 6D) and class II (6E, 6F) major histocompatibility complex in the IO/LD7/4 clone in the absence (6A, 6C, 6E) or presence (6B, 6D, 6F) of induction by IFN-γ, FIGS. 7A–7B show, for the IO/LD7/4 cells, the expression of the adhesion molecules ICAM-1 (7B, black bars) and VCAM-1 (7B, shaded bars) and the class II I-A histocompatibility antigens (7A, black) and I-E histocompatibility antigens (7A, shaded) in response to IFN-γ from 0 to 5 days;

FIG. 8 shows the migration of T-lymphocytes across monolayers consisting of the primary cultures of retinal endothelial cells (REC), retinal pigmentary epithelial cells (RPE) or the IO/JG2/1 and IO/LD7/4 clones;

FIG. 9 shows electron micrographs of IO/LD7/4 cells co-cultivated with dissociated retina; the debris of external segments (ROS) is adjacent to the cells and found in the phagosomes (P);

FIG. 10 shows IO/LD7/4 cells cultivated on slides coated with Matrigel®: the cells show a high contractile capacity, creating stress lines in the matrix;

FIG. 11 shows the hexagonal morphology of the cells obtained after grafting the IO/LD7/4 cells onto the retina of Sprague-Dawley rats;

FIGS. 12A–12D show the means and standard deviations of the latency times of the pupillary reflexes in response to a light stimulus in rats grafted with primary RPE cells (FIG. 12A) and with IO/LD7/4 cells (FIG. 12B) and in control animals (blank operation) (FIG. 12C); the data in FIG. 12D show the responses of a dystrophic RCS rat as a function of age; the mean latency time of a non-dystrophic rat is 0.48±0.04 second; L=left eye and R=right eye;

FIGS. 13A–13D show the means and standard deviations of the amplitude of the pupillary reflex responses to light in rats grafted with primary RPE cells (FIG. 13A) and with IO/LD7/4 cells (FIG. 13B) or in control rats (FIG. 13C); the data shown in FIG. 13D correspond to the responses of a dystrophic RCS rat as a function of age; the mean amplitude of response of a non-dystrophic 6-month-old animal is 19.7±5.7%; L=left eye and R=right eye;

FIG. 14 shows the modifications of the mean activity of rats placed in cages with walls of different designs; rats grafted with IO/LD7/4 cells (shaded bars), control rats (blank operation or sham; white bars); blank=plain walls; check=decorated walls;

FIG. 15 shows the number of active units of visual field in the superior colliculus, expressed as a percentage of the total number of recordings; the IO/LD7/4 and primary RPE cells are capable of slowing down the loss of visual field in the grafted animals compared with the non-grafted animals (control or sham);

FIG. 16 shows on the one hand a two-dimensional view of the superior colliculus (FIGS. 16A and 16B, in which C=caudal, M=medial, R=rostral and L=lateral), and on the other hand the maps of the corresponding visual fields of the retina (FIGS. 16C and 16D, in which D=dorsal, N=nasal, V=ventral and T=temporal); the crosses on the map of the colliculus represent the zones for which no recording could be obtained; the dots correspond to the zones for which recordings could be obtained; the left-hand Figures (FIGS. 16C and 16D) represent the recordings of a dystrophic 6-month-old rat: the recordings could be made from a single unit (light zone), which is typical of animals of this age. The right-hand Figures (FIGS. 16B and 1D) represent the recordings of a rat grafted with IO/LD7/4 cells on the superior temporal retina. It is observed that responses can be obtained from a wide zone of the colliculus;

FIGS. 17A–17D show some of the differences relating to the histological characteristics (number of nuclei in the outer nuclear layer: FIG. 17A; number of nuclei in the inner nuclear layer: FIG. 17B; depth of the external plexiform layer in $\mu$m: FIG. 17C; relative zone (%) of retinas saved by grafting: FIG. 17D) of the retinas of rats grafted with primary RPE cells or IO/LD7/4 cells.

FIG. 18 is an identification of the deposit of the immortalized retinal pigmentary epithelial cells called IO/LD7/4 on Apr. 18th 1996 in the Collection Nationale de Cultures de Micro-organismes held by the Institut Pasteur, 28 rue de Docteur Roux, 75724 PARIS CEDEX 15, under the identification no. I-1694. The indications in section B states (in French):

With regard to the nominations in which a European patent is applied for, until the publication of the mention of the grant of the European patent or until the date on which the application shall be refused or withdrawn or shall be deemed to be withdrawn, a sample of the deposited microorganism shall be available only by the issue of a sample to an expert nominated by the requester (Rule 28.4) of the EPC).

FIG. 19 is an identification of the deposit of the immortalized retinal endothelial cells called IO/JG2/1 on Apr. 18th 1996 in the Collection Nationale de Cultures de Microorganismes held by the Institut Pasteur, 28 rue de Docteur Roux, 75724 PARIS CEDEX 15, under the identification no. I-1695. The indications in section B states (in French):

With regard to the nominations in which a European patent is applied for, until the publication of the mention of the grant of the European patent or until the date on which the application shall be refused or withdrawn or shall be deemed to be withdrawn, a sample of the deposited microorganism shall be available only by the issue of a sample to an expert nominated by the requester (Rule 28.4) of the EPC).

It must be clearly understood, however, that these Examples are given solely in order to illustrate the subject of the invention, without in any way implying a limitation.

EXAMPLE 1

Methods Used to Characterize the Immortalized Cells According to the Invention a) Isolation and Culture of Rat Aortic Endothelial Cells The aortic endothelium is isolated by the method described by McGUIRE P. G. et al. (Lab. Invest., 1987, 57, 94–105).

The rat aorta is removed by dissection and cut into small pieces (2–5 mm), which are placed on 24-well plates coated with collagen and containing an endothelial cell culture medium, in such a way that the luminal face of the pieces of aorta is in contact with the collagen.

The RPMI culture medium is supplemented with 20% of foetal calf serum, 7.5 $\mu$g/ml of endothelial cell growth supplement, 80 $\mu$g/ml of heparin, 2 mM glutamine, 0.5 $\mu$g/ml of vitamin C, 100 U/ml of penicillin and 100 $\mu$g/ml of streptomycin.

After 3 days, the explants are removed and the adhering cells proliferate to the point of confluence. At confluence, the cells have a pavement morphology characteristic of the endothelial vessels, express Von Willebrand's factor and proliferate in a medium containing D-valine.

The cells are used after three passages (earliest stage for experimental use).

b) Protocol for Carrying Out Electron Microscopy for the Morphological Study of the Different Cells Obtained The monolayers of the immortalized cells (retinal endothelial cells and RPE cells) are cultivated in 24-well plates to the point of confluence. The cells are fixed with a mixture of 1% of paraformaldehyde and 3% of glutaraldehyde in 0.1 M sodium cacodylate HCl (pH 7.4), or 2.5% of glutaraldehyde in 0.1 M sodium cacodylate buffered to pH 6.9 by the addition of 0.5% (w/v) tannic acid.

After rinsing 3 times for 5 minutes in a sodium cacodylate buffer (pH 7.4), the cells are fixed again for 2 hours at 4° C., in the absence of light, in 1% aqueous osmium tetroxide solution, dehydrated in the presence of different strengths of alcohol (1×10 min 50–90%, 4×10 min 100%), included in Araldite and cured at 60° C. for 12 hours. Semi-thin (1 $\mu$m) and ultra-thin (50 nm) sections are prepared using a Leica Ultracut S® microtome. The semi-thin sections are stained with 1% toluidine blue in 50% ethanol for microscopic observation and the ultra-thin sections are stained sequentially with 1% lead citrate in 50% ethanol and with lead citrate and are observed and photographed with a JEOL 1010 transmission electron microscope operating at 80 kV.

c) Protocol for Detecting the Endothelial and Epithelial Surface Antigens by ELISA, Immunohistochemistry and Flux Cytometry

ELISA:

Rat retinal endothelial cells (primary culture and immortalized cells) are inoculated at confluence density onto 96-well plates which have first been coated with 0.05% type IV collagen.

Before the cells are plated, the collagen is fixed in ammonia vapour and the plates are washed twice with HBSS. The cells are cultivated for 3 days before experimental use. After the experimental treatments, the cells are washed 4 times in Hanks' buffered saline solution (HBSS) and fixed with 0.1% of glutaraldehyde in phosphate buffered saline (PBS) for 10 minutes at room temperature.

The cells are washed with 50 mM Tris-HCl buffer, pH 7.5, for 20 minutes at room temperature. The primary antibodies are diluted in 100 $\mu$l of HBSS containing 100 $\mu$g/ml of normal rabbit IgG and 4 mg/ml of bovine serum albumin and then incubated with the cells for 45 minutes at 37° C. The cells are washed 4 times with PBS containing 0.2% of Tween 20 and then incubated with a biotinylated anti-mouse IgG (1:700; Amersham) for 45 minutes at 37° C. The cells are washed again 4 times with PBS containing 0.2% of Tween 20 and incubated with horseradish peroxidase/streptavidine (1:700; Amersham) for 45 minutes at 37° C. The cells are washed 4 times in PBS containing 0.2% of Tween 20 and incubated with 100 $\mu$l of tetramethylbenzidine in a citrate-acetate buffer (pH 5) for 10 minutes. The reactions are stopped by the addition of 50 $\mu$l of 1 M sulphuric acid and the reaction product is quantified (optical density at 450 nm).

* Histochemical studies:

The primary cultures and immortalized cells are inoculated onto slides (Gibco/BRL) and cultivated to the point of confluence.

The surface antigens are detected by washing the cells in HBSS and then blocking with HBSS containing 100 $\mu$g/ml of normal rabbit IgG and 4 mg/ml of bovine serum albumin.

The primary antibodies are then added to the non-fixed cells, the cells are incubated for 1 hour on ice and washed, a second, specific biotinylated antibody is added and the cells are incubated for 30 minutes. After washing, FITC-labelled streptavidine is incubated with the cells for 15 minutes. The cells are then fixed, mounted and observed under a Zeiss Axiophot. For the intracellular antigens, the cells are fixed and rendered permeable as described for the ELISA method.

* Flux cytometry:

The flux cytometry of the confluent retinal cultures is carried out on a FACScan apparatus (Becton-Dickinson). After washing, the cellular monolayers are dissociated in HBSS containing 1 mg/ml of collagenase/dispase and 0.2% of EDTA and the cells are resuspended in PBS.

$5.10^4$ cells/flask are incubated for 1 hour with the primary antibody on ice, this being followed by a second incubation for 1 hour with an anti-mouse IgG rabbit F(ab')$_2$ antibody conjugated with FITC, in the presence of 20% of normal rat serum. After 2 washes, the cells are resuspended in PBS and analyzed. The non-stained cells are used for calibration and the cells stained only with the second antibody are used to establish the background.

d) Protocol for Studying the Migration of the T-lymphocytes Across the Monolayer The capacity of the immortalized cells to allow the trans-endothelial migration of the T-cells specific for the antigen is determined as described in GREENWOOD J. et al. (Immunol., 1993, 80, 401–406).

The T-cells ($2.10^5$ cells/ml/well) are introduced into 24-well plates containing monolayers of primary cell culture or immortalized retinal endothelial cells and RPE cells.

The T-cells sediment and migrate in 4 hours. To evaluate the migration rate, the co-cultures are placed under a phase contrast microscope and maintained at 37° C. and in an atmosphere containing 5% of $CO_2$.

A 200×200 μm field is chosen at random and recorded for 10 minutes, spread out over a 4-hour period, with a camera. The data are expressed as the percentage of total lymphocytes in a field which have migrated across the monolayer; a minimum of 6 wells/test are analyzed.

EXAMPLE 2

Preparation of a Line According to the Invention: Rat Retinal Endothelial Cells a) Isolation and Culture of the Retinal Endothelial Cells Endothelial cells are derived from 4- to 6-week-old female Lewis rats free of pathogens. The retinal cells are isolated and cultivated by the methods described by GREENWOOD J. (J. Neuroimmunol., 1992, 39, 123–132) and ABBOTT N. J. et al. (Cell Sci., 1992, 103, 23–37). These techniques produce primary cultures with a purity in excess of 95%. The rat retinas are dispersed by enzymatic digestion, the fragments of microvessels are separated from the cells themselves by centrifugation and the cells are washed and cultured in flasks coated with collagen. The growth medium consists of Ham's F-10 medium (Sigma) supplemented with 17.5% of serum (Advanced Protein Products Ltd), 7.5 μg/ml of endothelial cell growth supplement (Advanced Protein Products Ltd), 80 μg/ml of heparin, 2 mM glutamine, 0.5 μg/ml of vitamin C, 100 U/ml of penicillin and 100 μg/ml of streptomycin.

The cultures are maintained at 37° C. and in an atmosphere containing 5% of $CO_2$; the medium is replaced every three days to the point of confluence.

b) Immortalization of the Cells

A retroviral vector containing the SV40 T-gene, which is replication-deficient and obtained according to the technique described by P. S. JAT et al. (Mol. Cell. Biol., 1986, 1204–1217), is produced in quantity in selected fibroblast lines (SVUI9.5 line).

This retroviral vector codes in particular for a tsa58 T-antigen, which is temperature-sensitive and associated with the gene coding for neomycin as a selection marker. It is obtained from the culture supernatant of SVU19.5 cells after passage through a 0.45 μm filter to remove the producer cells. It is added to a primary culture of endothelial cells such as those prepared in a) (transfection).

200 μl of virus in 2 ml of a medium containing 8 μg/ml of Polybrene (Aldrich) are added to the endothelial cells; the whole is incubated for 4 hours at 37° C. in an incubator under a $CO_2$ atmosphere, the flask being shaken every 15 minutes.

After incubation, the medium is removed and 5 ml of fresh medium are added; the whole is recultivated overnight. The cells are then kept in the incubator for 48 hours. They are then plated on a selective medium containing 200 μg/ml of geneticin (G418, Gibco) and the immortalized parental lines are obtained by selection of the resistant colonies. Cloning by limiting dilution of the parental line gives particularly the selected IO/JG2/1 clone for a more thorough study.

c) Characteristics of the IO/JG2/1 Clone

This clone is cultivated up to the thirtieth passage without significant morphological or phenotypic differences.

Morphology

Figure 1A:
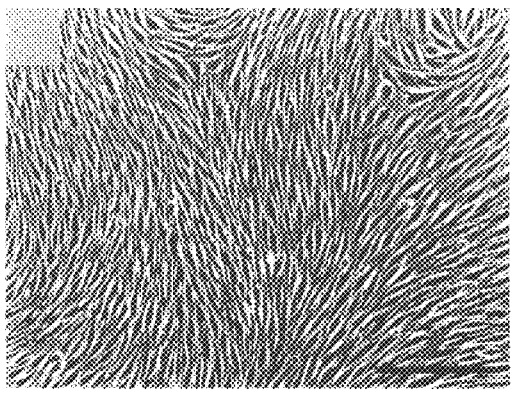
Figure 1B:
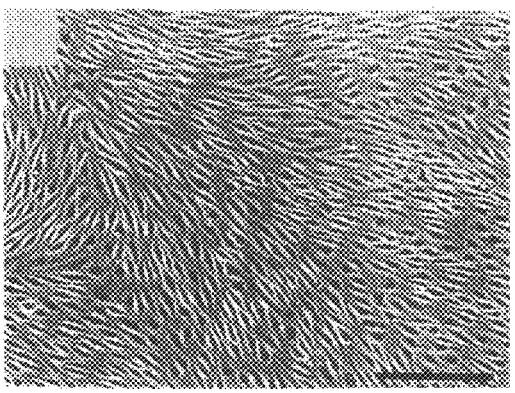

The primary cultures of retinal endothelial cells have a fusiform morphology characteristic of these cells (FIG. 1A). The immortalized IO/JG2/1 clone conserves this characteristic morphology (FIG. 1B).

Ultrastructural appearance

Figure 2A:
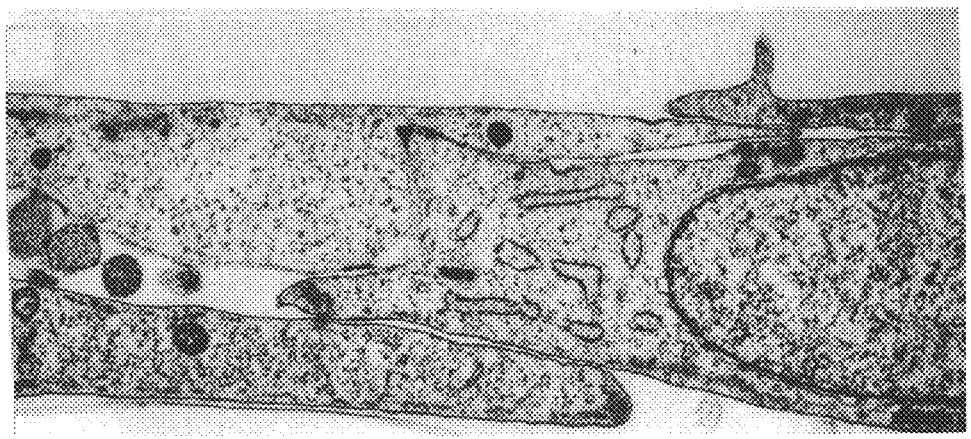
Figure 2B:
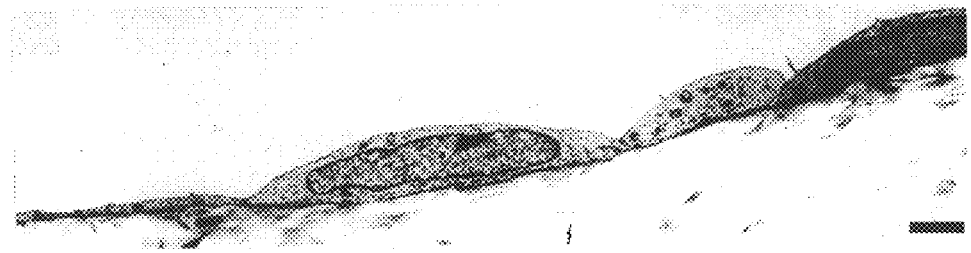
Figure 2C:
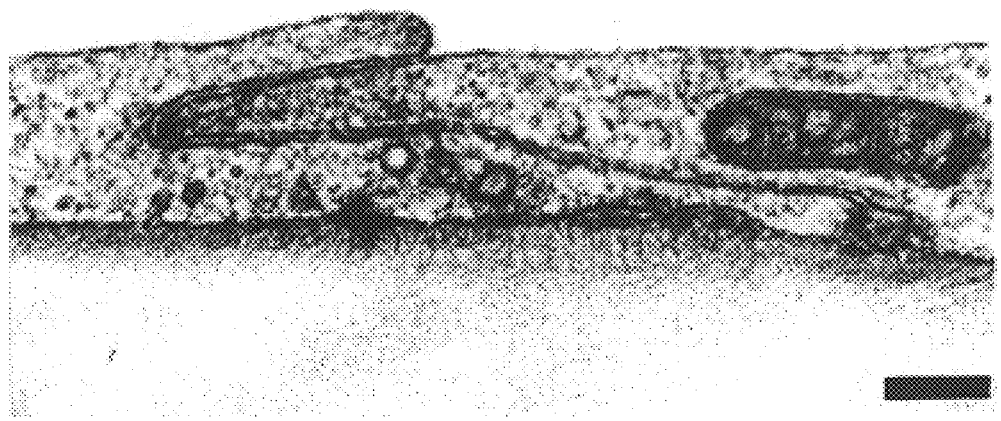

The ultrastructural appearance of the IO/JG2/1 clone (FIG. 2: B, C) is similar to that of the primary cultures. A voluminous nucleus is observed together with the presence of peripheral heterochromatin and numerous cytosolic organelles such as mitochondria, endoplasmic reticulum and polysomes. The junctions between the cells often exhibit interdigitation with regions of cytoplasmic density at the narrow points of contact. The cells rest on a lamina basalis.

Expression of the tsa58 T-antigen

Figure 3A:
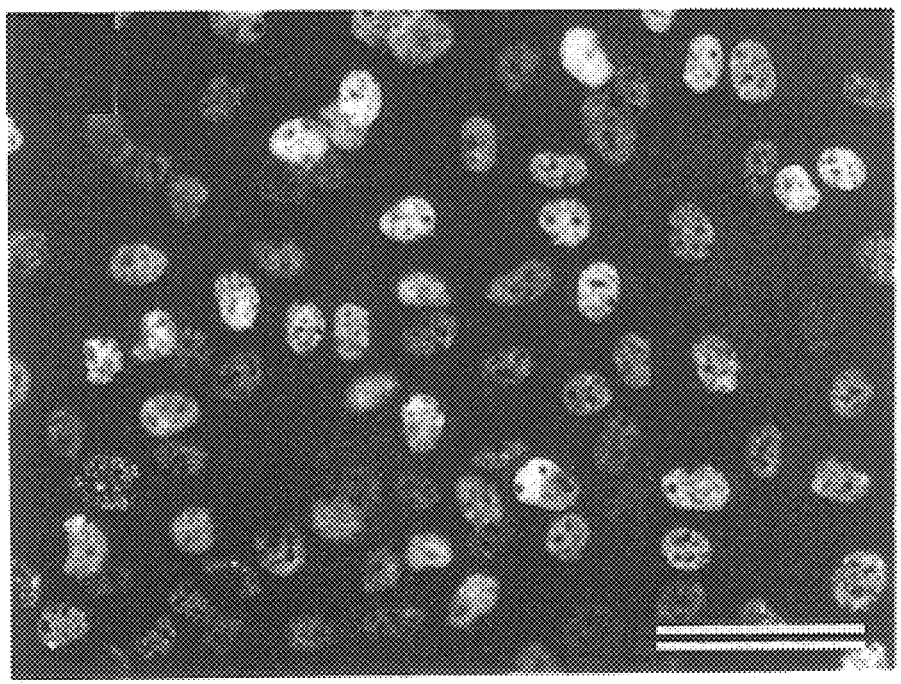
FIGS. 3A–3B show the nuclear staining obtained in the presence of antibodies directed against the T-antigen: IO/JG2/1 (3A) and IO/LD7/4 (3B)
Figure 3B:
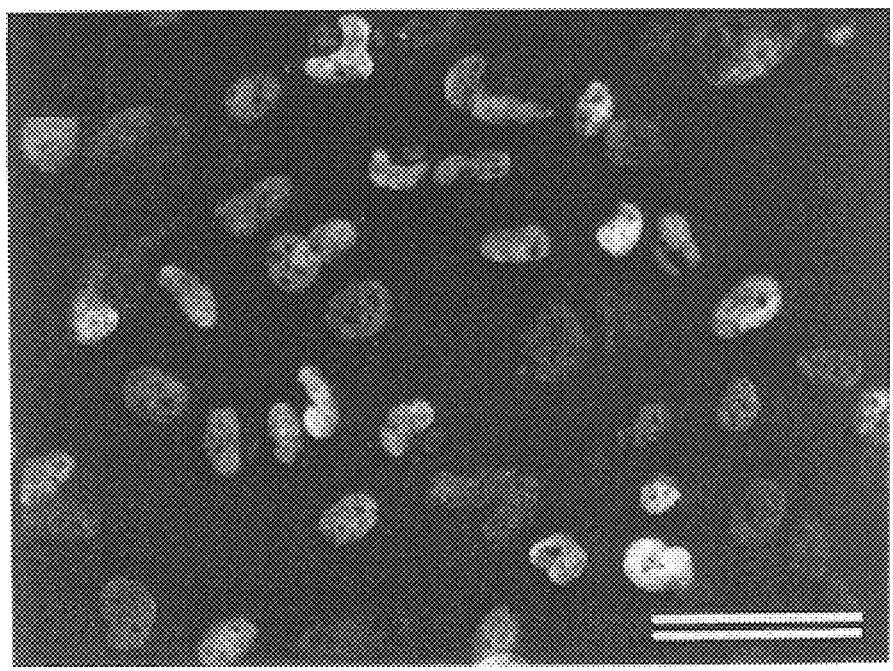
Figure 4A:
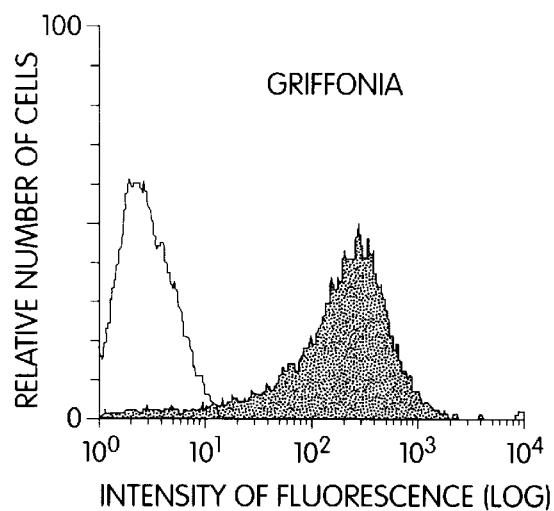
FIGS. 4A–4F show the expression of different endothelial markers in the IO/JG2/1 cultures (4A–4F)
Figure 4B:
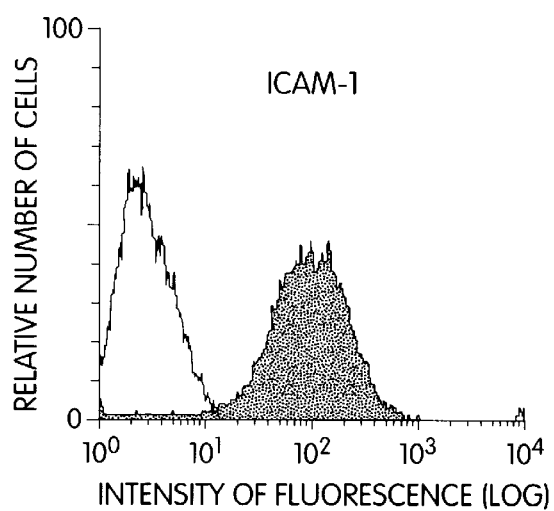
Figure 4C:
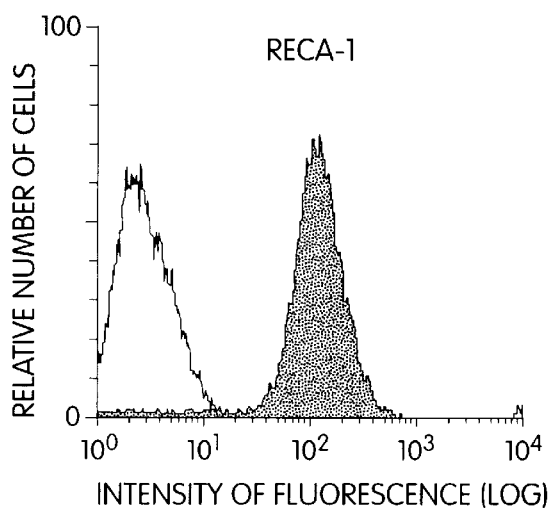
Figure 4D:
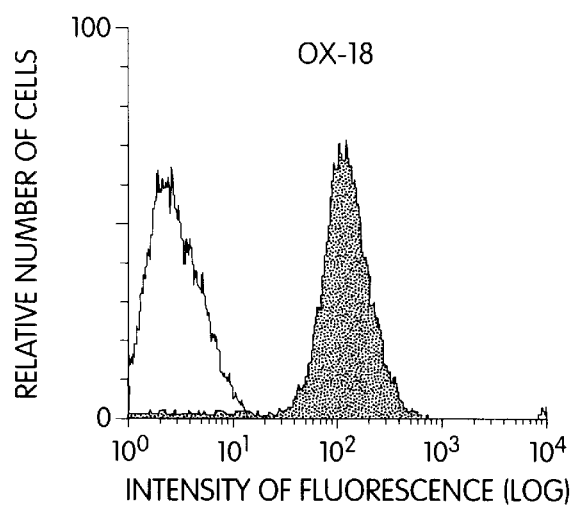
Figure 4E:
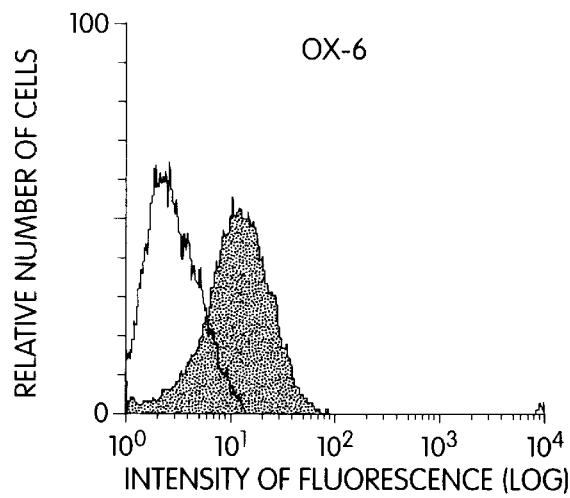
Figure 4F:
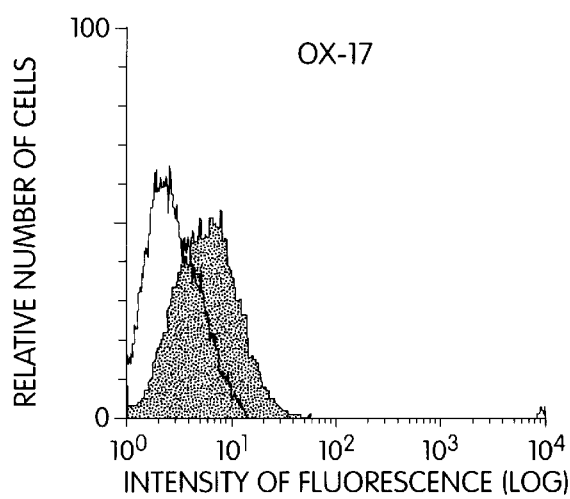
Figure 5A:
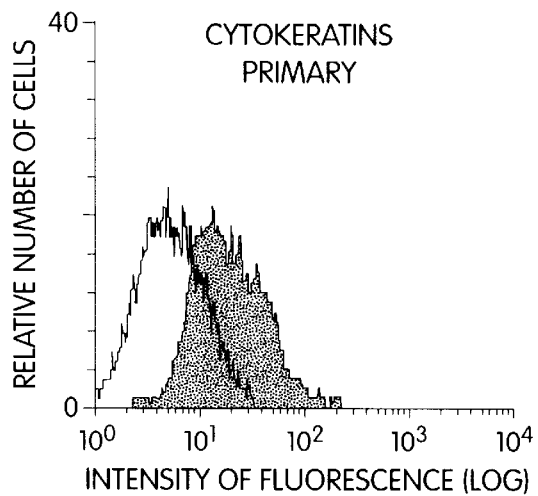
FIGS. 5A–5D show the comparative expression of different epithelial markers in the primary cultures (5A, 5B) and the IO/LD7/4 clone (5C, 5D)
Figure 5B:
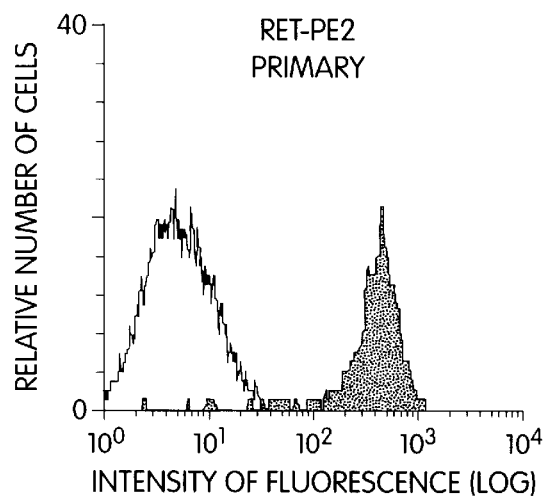
Figure 5C:
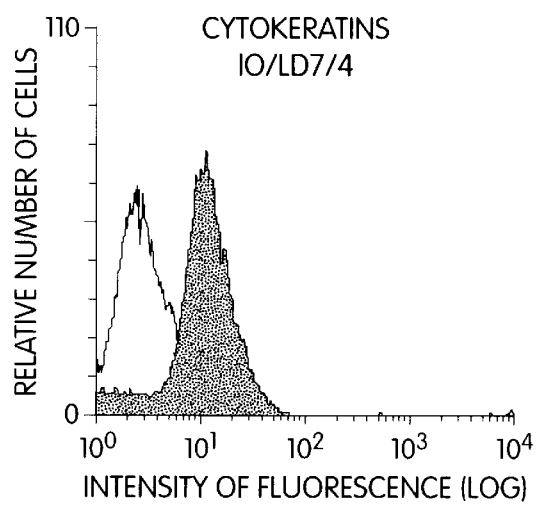
Figure 5D:
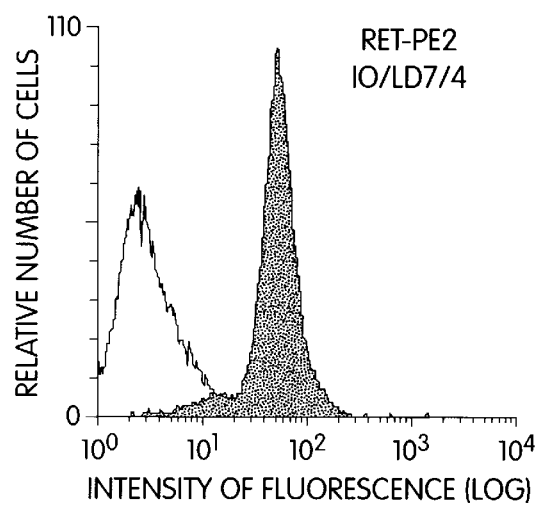
Figure 6A:
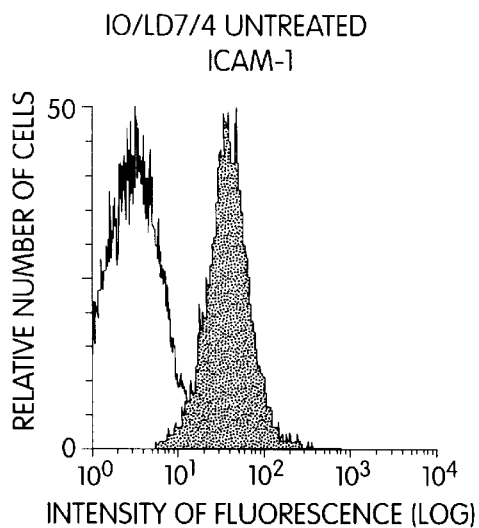
Figure 6B:
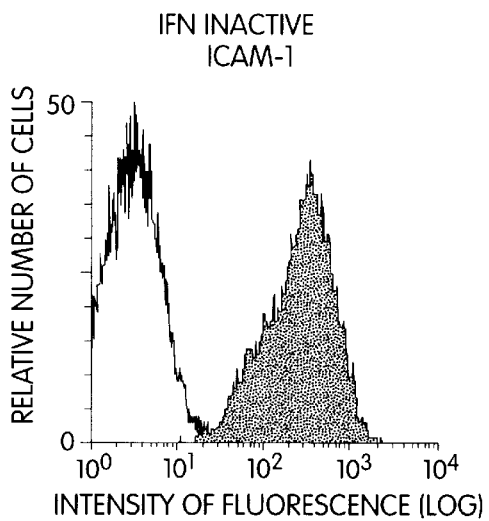
Figure 6C:
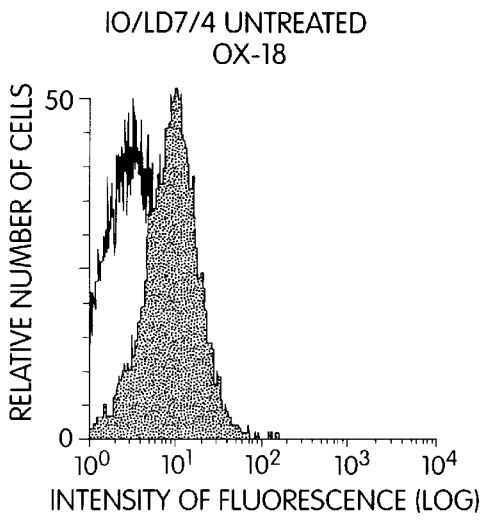
Figure 6D:
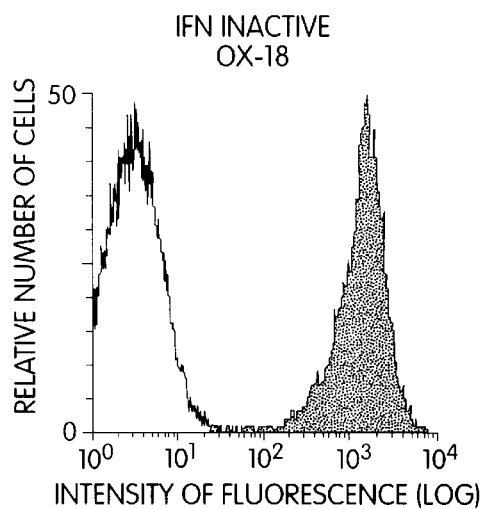
Figure 6E:
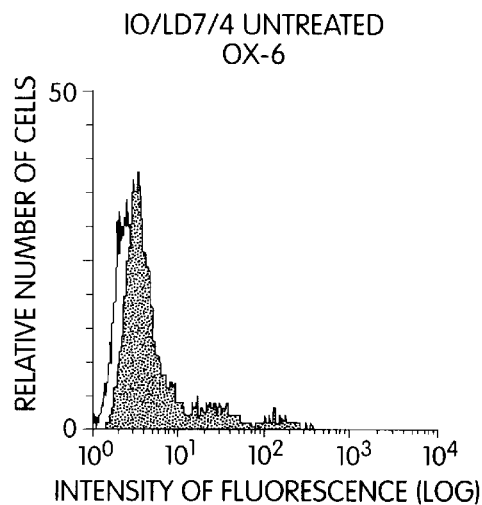
Figure 6F:
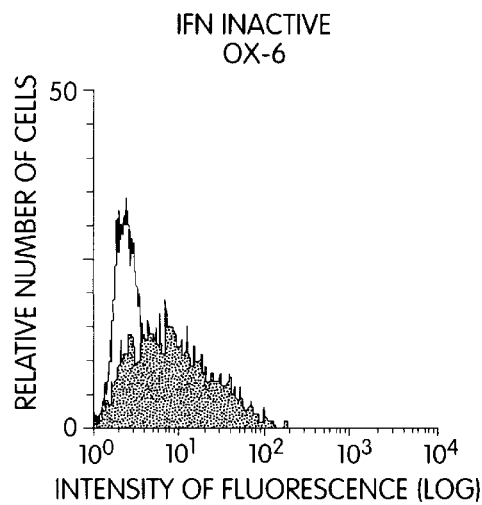

All the immortalized retinal endothelial cells selected in the G418 medium show substantial nuclear staining with antibodies directed against the T-antigen (FIG. 3A: IO/JG2/1; FIG. 3B: IO/LD7/4), whereas no staining is observed in the endothelial cells of the primary cultures.

Expression of endothelial markers

The IO/JG2/1 clone expresses a number of antigens specific for the endothelial cells; the results obtained are illustrated in Table I.

TABLE I

| Antigen | REC primary | | | IO/JG2/1 clone | | | CEC primary | | | Aortic EC | | |
|---|---|---|---|---|---|---|---|---|---|---|---|---|
| | Base level | IFN | TNF | Base level | IFN | TNF | Base level | IFN | TNF | Base level | IFN | TNF |
| P-glycoprotein (JSB-1) | + | nd | nd | + | nd | nd | + | nd | nd | − | nd | nd |
| GLUT-1 | + | nd | nd | + | nd | nd | + | nd | nd | − | nd | nd |
| Von Willebrand's factor | + | nd | nd | + | nd | nd | + | nd | nd | + | nd | nd |
| Transferrin receptor (OX-26) | + | nd | nd | (+) | nd | nd | + | nd | nd | − | nd | nd |
| RECA-1 | + | nd | nd | + | nd | nd | + | nd | nd | nd | nd | nd |
| ICAM (3H8/1A29) | + | + | + | + | + | + | + | + | + | + | + | + |
| VCAM-1 (5F10) | − | + | + | − | + | + | − | + | + | + | + | + |
| PECAM-1 | + | nd | nd | + | nd | nd | + | nd | nd | + | nd | nd |
| Non-EC CNS (OX-43) | − | nd | nd | − | nd | nd | − | nd | nd | + | nd | nd |
| CD44 (OX-50) | + | nd | nd | + | nd | nd | + | nd | nd | + | nd | nd |
| Class I MHC (OX-18) | + | + | + | + | + | + | + | + | + | + | + | + |
| Class II I-A MHC (OX-6) | − | (+) | − | − | + | − | − | + | − | − | + | − |
| 3H12B | + | + | + | (+) | + | + | + | + | + | + | + | + |
| 4A2 | + | + | + | + | + | + | + | + | − | + | + | + |

EC CNS = Endothelial cells of the central nervous system
REC primary = retinal endothelial cells in primary culture
CEC primary = cerebral endothelial cells in primary culture Table I shows in particular that this clone expresses especially Von Willebrand's factor, the REC-1 antigen, the ICAM-1 antigen, the expression of which can also be induced by treatment with 100 U/ml of IFN-γ or TNFα for 24 hours (Table I and FIGS. 4 and 6), and the VCAM-1 antigen, after induction by the above-mentioned cytokines (200 U/ml of IFN-γ or TNF for 24 hours or 48 hours) (cf. Table I).

Expression of endothelial markers specific for the CNS

Table I also shows that the IO/JG2/1 clone constitutively expresses a number of markers specific for the endothelial cells of the CNS, especially P-glycoprotein, GLUT-1 and the transferrin receptor (cf. Table I); however, the IO/JG2/1 clone does not express some of the antigens specific for the cerebral endothelial cells, especially the 1A8B and 2A4 antigens, making it possible to differentiate it from the cerebral endothelium (Table II below).

Comparison of the expression of the endothelial antigens in the primary cultures and the immortalized lines with the peripheral endothelial cells As stated above, the primary cultures of retinal endothelium and the derived clones expressing the T-antigen show a constitutive expression of the markers specific for the endothelial cells of the CNS, namely P-glycoprotein, GLUT-1 and the transferrin receptor (Table I), whereas the aortic endothelium does not express these antigens but does express the OX-43 antigen, which is considered to be specific for the peripheral endothelial cells; the OX-43 antigen is effectively not expressed either by the primary cultures or by the immortalized cultures of cerebral and retinal endothelial cells (Table I).

These different cultures were also screened against a sample group of antigens considered to be specific for the cerebral endothelial cells. The results are illustrated in Table II.

TABLE II

| Antigen | REC primary | IO/JG2/1 clone | CEC primary | Aortic EC |
|---|---|---|---|---|
| 3B7 | + | − | + | + |
| 3D11 | + | + | + | + |
| 3D7B | + | (+) | + | + |
| 4C6C | + | (+) | + | + |
| 2F1B | + | + | + | + |
| 2A4 | − | − | + | + |
| 4E3 | + | + | + | + |
| 2A5 | + | + | + | + |
| 1A8B | − | − | + | + |
| 1C1 | + | − | + | + |
| 1C11 | + | + | + | + |
| 1D2 | + | − | + | + |
| 4E8.C4 | + | + | + | + |

Expression of the antigens of the major histocompatibility complex

All the endothelial cultures show a constitutive expression of the class I major histocompatibility antigens (OX-18, cf. Table I and FIGS. 4, 6 and 7), which is induced by 100 U/ml of rat recombinant IFN-γ for 24 hours.

The primary cultures of retinal and cerebral endothelial cells, and the parental lines and the clones expressing the T-antigen, show very little or no expression of the class II major histocompatibility antigens.

Cultures of endothelial cells treated for 24 hours only with 100 U/ml of recombinant WFN-γ exhibit a substantial induction of certain class II antigens: OX-6 and OX-17 (cf. Table I and FIG. 4).

Migration of the T-lymphocytes across the monolayer

No significant difference exists between the capacity of the primary cells and that of the immortalized cells to support specific T migration. The degree of migration across the monolayers in the course of a 4-hour test is 52±5% for the cerebral primary endothelial cells, 48±4% for the retinal primary endothelial cells and 54±6% for the IO/JG2/1 retinal endothelial clone (FIG. 8).

EXAMPLE 3

Preparation of a Line According to the Invention:
Rat Retinal Epithelial Cells a) Isolation and Culture of the Retinal Pigmentary Epithelial Cells The rat retinal pigmentary epithelial cells are isolated from 6- to 8-day-old PVG rats according to the method of CHANG et al. (Curr. Eye Res., 1991, 10, 1081–1086). The eyes are removed and the intact eyeballs are digested with 2% dispase for 30 minutes. The eyes are then dissected for removal of the cornea and the vitreous body; the retina is then isolated and incubated for 15 minutes in a culture medium. After incubation, layers of retinal pigmentary epithelial cells (RPE cells) are separated from the neuroretina and treated with trypsin to produce a cellular suspension. The cells are plated in tissue culture flasks and cultivated to the point of semiconfluence. The culture medium consists of Ham's F-10 medium supplemented with 20% of foetal calf serum, 20 mM HEPES, 7.5% of sodium bicarbonate, 2 mM glutamine, 100 U/ml of penicillin and 100 $\mu$g/ml of streptomycin. These primary cultures grow in the form of pigmented monolayers which are positive for the cytokeratins and the epitope specific for the RPE, namely RET-PE2 (NEILL et al., Exp. Eye Res., 1990, 51, 573–583).

b) Immortalization of the Cells

These cells are prepared under the same conditions as those described in Example 2, with the exception of the incubation time with the retroviral vector, which is 2 hours. The immortalized parental lines are obtained by selection of the resistant colonies. Cloning by limiting dilution of the parenteral line gives in particular the IO/LD7/4 clone, which is selected for a more thorough study.

c) Characteristics of the IO/LD7/4 Clone

This clone is cultivated up to the 52nd passage with no significant morphological or phenotypic differences.

Morphology

Figure 1C:
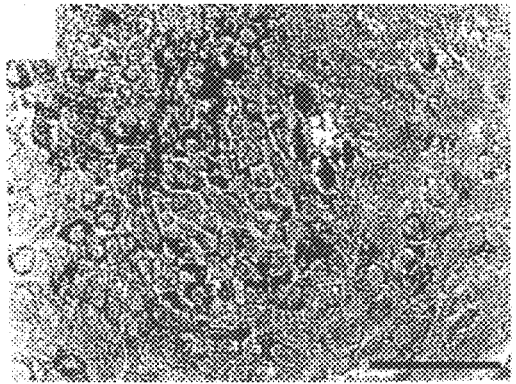
Figure 1D:
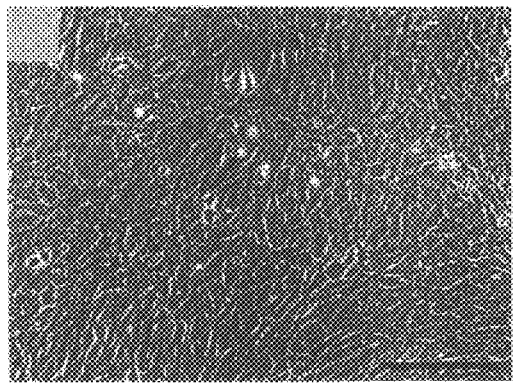

The morphology of the immortalized RPE cells (FIG. 1D) is similar to that of the primary cultures (FIG. 1C). In contrast to the primary cultures, the immortalized cells are not pigmented.

Ultrastructural appearance

Although the immortalized cells of the IO/LD7/4 clone are not pigmented when observed under the microscope, the TEM reveals dense bodies with the appearance of premelanosomes (FIG. 2A).

Expression of the tsa58 T-antigen

The immortalized RPE cells selected with the aid of G418 show substantial nuclear staining in the presence of antibodies directed against the T-antigen (FIG. 3B), whereas no staining is observed with the RPE cells in primary cultures.

Expression of RPE markers

The primary cultures of RPE cells and the immortalized IO/LD7/4 clone express the antigen specific for the RPE cells, namely RET-PE2 (FIG. 5). Furthermore, the expression of the cytokeratins, which are normally used to identify RPE cells, is present to the same extent in both the primary cultures and the immortalized cells, as illustrated in the flux cytometry analysis (FIG. 5).

Expression of the antigens of the major histocompatibility complex

All the pigmentary epithelial cultures show a constitutive expression of the class I major histocompatibility antigens (OX-18, cf. Table I and FIGS. 4, 6 and 7), which is induced by 100 U/ml of rat recombinant IFN-$\gamma$ for 24 hours.

Both the primary cultures and the immortalized RPE cells are incapable of expressing the antigens of the class II I-A or class II I-E major histocompatibility complex; however, after 5 days of activation, there is a weak but significant expression of both I-A (FIGS. 6 and 7) and I-E.

Expression of the adhesion molecules

The primary and immortalized RPE cell cultures do not constitutively express VCAM-1, but after 3–5 days of activation with IFN-$\gamma$, low levels of expression are observed (FIG. 7).

Migration of the T-lymphocytes across the monolayer

The migration across the monolayers of primary and immortalized RPE cells differs significantly: the primary cells exhibit a degree of migration (38±3%) which is significantly greater than that of the immortalized IO/LD7/4 cells (17±2%, p<0.01) (FIG. 8).

d) Phagocytosis of External Segments of the Rods by the IO/LD7/4 Cells in vitro

Method:

IO/LD7/4 cells are cultivated to the point of confluence on Thermanox® slides in 4 wells of tissue culture plates. The medium is sucked off and replaced with a medium containing a suspension of dissociated adult retinal cells. 24 hours later, the retinal suspension is removed and then the slides are rinsed and treated for observation under the electron microscope. The cells are also cultivated on slides coated with Matrigel®, rinsed, fixed and stained with cresyl violet.

Results:

The presence of retinal material (external segments of photoreceptors) dissociated in the phagosomes can be distinguished in the electron micrographs of IO/LD7/4 cells.

External segments can be identified both in suspension above the primary RPE cells and in the phagosomes. A thin layer of electronically dense material can be observed under the layer of cells in culture and is interpreted as corresponding to a basal membrane produced by the cells (FIG. 9).

The cells cultivated on Matrigel® cause a contraction of the matrix (FIG. 10).

EXAMPLE 4

Implantation of IO/LD7/4 Cells in the Subretinal Space

The immortalized RPE cells according to the invention can be implanted in the subretinal space; they make it possible to save the photoreceptors from degeneration and constitute a particularly advantageous source of production of donor cells.

1. Pilot Experiment: Grafting of IO/LD7/4 Cells in Sprague-Dawley Rats and RCS Rats Methods Immortalized cells according to the invention (IO/LD7/4 cells) are injected into the subretinal space of 8 anaesthetized 12-week-old Sprague-Dawley rats and six 4-week-old RCS rats.

The eye is rotated towards the nose and anchored; an incision is made with a very fine scalpel (microsurgical knife with an angle of 15°) through the scleroid and choroidal layers in order to facilitate the insertion of a micropipette. The cells ($2.10^4/\mu l$) are injected into the subretinal space using a micropipette attached to a 10 $\mu l$ Hamilton syringe.

Half the group is treated orally with cyclosporin (2.1 mg/rat/day) throughout the experiment.

The rats in each group are anaesthetized with a lethal dose of anaesthetic (Euthatal®) and then an intracardiac perfusion is carried out successively with PBS and a tissue fixative; the animals are then enucleated.

The eyes are cryoprotected and included in OCT® (Miles) (cryoprotection agent).

A series of sections are prepared (14 $\mu$m thick) and stained with cresyl violet and with a monoclonal antibody directed against the SV40 T-antigen and against PCNA (proliferative cell nuclear antigen).

Results

No tumour formation is observed in the eyes of animals which have received grafts of IO/LD7/4 cells.

No immune response is observed in the eyes of animals which have not received an immunosuppressive treatment.

In the majority of sections, the epithelial cell layer is a single layer (monolayer), but a multilayer is observed in certain regions.

When the blocks were sectioned <<face-on>>, the immortalized cells according to the invention possessed in vivo the hexagonal phenotypic characteristics of the primary RPE cells, even though these characteristics were lost in vitro (FIG. 11); this is obvious when the transplant has more than one layer of cells.

Protection of the photoreceptors is observed in all the retinas of RCS rats which have grafts of IO/LD7/4 cells. All the sections stained with the antibodies directed against the SV40 T-antigen and PCNA are negative.

2. Comparison Between Grafts of Freshly Harvested Primary RPE Cells and Grafts of IO/LD7/4 Cells on the Visual Function Methods 11 dystrophic RCS rats (3–4 weeks old) are grafted either with primary RPE cells or with IO/LD7/4 cells by injection into the subretinal space of each eye, as described in 1.

A separate group of animals is injected with medium only (control operation).

a) Evaluation of the Pupillary Light Reflex (PLR)

The PLR is recorded with a pupillometer 6 months after transplantation; the animals are tested under anaesthetic (halothane/nitrous oxide).

The light stimulus is presented for 3 seconds; the data are collected with an ISCAN pupillometer and the latency and amplitude of the response are recorded.

Results

The latency time of the PLR responses of the animals which have received a graft of IO/LD7/4 cells is significantly shorter than that of the animals which have received a graft of primary RPE cells or an injection of medium (FIG. 12).

The amplitude of the responses exhibits large variations in the different groups; however, a subset of animals which have received IO/LD7/4 cells shows a greater amplitude of response than the other groups (FIG. 13).

b) Behavioural Evaluation of the Visual Acuity

To evaluate the capacity of the rats to detect visual images, the rats are placed in a large cage whose walls can be changed (plain walls or decorated walls).

2 rats are present in each cage during the test; their activity is measured for 5 minutes.

In a first stage, the animal explores its environment but gets accustomed to it.

In a second stage, the activity of the animal increases only if the walls are changed; in fact, if the visual environment is the same, the activity is not modified.

The extent of the animal's activity can consequently be used as an index of its visual detection and its visual acuity.

Results

The capacity of the dystrophic rats to detect the variations in their visual environment decreases over a period of 3 months.

The exploratory activity of the rats grafted with IO/LD7/4 cells is high in the second part of the test, i.e. when the environment has been modified (plain walls changed to decorated walls or vice-versa) (FIG. 14).

c) Electrophysiological Evaluation

The head and eyes of the anaesthetized rats are immobilized by means of a stabilizing apparatus and sutures, respectively. The superior colliculus contralateral to the stimulated eye is exposed. The animals are adapted to a light level of 0.34 $cd/m^2$ for 1 hour before recording in order to enable the cones and rods to be evaluated simultaneously. The rat is orientated to face a translucent hemisphere (radius of 55 cm) so that the tested eye is at the centre. The stimuli, comprising a fixed light 10° in diameter and 5.8 $cd/m^2$ in intensity, are projected onto the surface of the hemisphere.

Different receptive fields (multi-unitary or single) are recorded from the layer nearest the surface of the superior colliculus (SC) (about 200 $\mu$m from the surface of the SC) using glass-coated carbon fibre electrodes.

The recordings cover the whole of the SC on the basis of a grid system with a pitch of 200 $\mu$m (FIGS. 15 and 16).

Results

The axons of the retina project onto the SC in a precise and well-defined manner; consequently, modifications in the recordings obtained from the SC do indeed reflect the changes which have occurred in the retina (FIG. 15).

A small scotoma begins to develop after 6 weeks in the dystrophic rats; it occupies half the visual field after 3 months and includes the whole of the retina after 6 months.

The primary RPE and IO/LD7/4 grafts slow down this deterioration of the visual field.

The grafts of IO/LD7/4 cells appear to be the more effective.

d) Morphological Evaluation of the Prevention of the Loss of Photoreceptors After the Grafting of Primary RPE Cells 4 eyes which had received either primary RPE cells or IO/LD7/4 cells were examined.

Using an image analysis software in association with a microscope (DMR, Leica), the thickness of each of the cellular layers of the retina is measured on the dystrophic 6-month-old rats and the number of nuclei in the inner and outer nuclear layers is counted.

The proportion of retina saved is estimated.

Results

After 6 months, no layer of photoreceptors is observed in the dystrophic rats. A few cells exist in the inner nuclear layer and can be considered as vestiges of photoreceptors.

The grafts of immortalized cells show large regions of saved cells in 6-month-old animals.

The proportion of retinal zone saved by the grafts of primary RPE cells is 6% and 13.8% with an outer nuclear layer (ONL) having a thickness equal to 3 strata of nuclei, whereas the percentage of retina saved by the grafts of IO/LD7/4 cells is 27.9% and 36.3% with an ONL having a thickness equal to 5 strata of nuclei.

An important difference between these sections is the presence of a distinct external plexiform layer in the eyes grafted with IO/LD7/4 cells (FIG. 17).

3. Migration of the IO/LD7/4 cells in vivo

Method 15 dystrophic 4-week-old rats are grafted with fluorescent IO/LD7/4 cells.

10 of the recipient rats are grafted on both eyes; the other 5 rats are grafted on one eye only.

The animals (2 with a transplant on both eyes and one with a transplant on one eye only) are sacrificed 3, 7, 14, 28, 42 and 98 days after grafting by administration of a lethal dose of anaesthetic (intracardiac perfusion in the presence of PBS).

The animals are enucleated and the eyes are fixed in 4% paraformaldehyde for 6 hours.

The tissue is cryoprotected and included in OTC.

Sections are prepared (14 μm thick) and made up into 3 series.

Series A is stained with cresyl violet; series B is stained with an antimicroglia antibody; the series are examined under a fluorescence microscope.

Results

The labelled cells are located in all the grafted eyes up to 14 days after the operation, but are more difficult to identify later because of elimination of the marker.

If the staining is clearly visible, the labelled cells occupy up to 30% of the retina.

Staining of the adjacent sections with cresyl violet confirms the action of the grafts on the saving of photoreceptors in all the transplants.

As is apparent from the foregoing description, the invention is in no way limited to those modes of execution, embodiments and modes of application which have now been described more explicitly; on the contrary, it encompasses all the variants thereof which may occur to those skilled in the art, without deviating from the framework or the scope of the present invention.

We claim:

1. An injectable, stable, immortalized, non-tumorigenic PVG rat retinal pigmenty epithelial cell line,
   (a) wherein the cells of the cell line comprise a polynucleotide comprising a heat-sensitive SV40 tsa58 T-antigen oncogene, and
   (b) wherein the cells of the cell line can non-tumorigenically integrate into a retina of a mammalian host.

2. The cell line of claim 1, wherein the cell line is IO/LD/7, deposited under no I-1694 on Apr. 18, 1996 in the Collection Nationale de Cultures de Micro-organismes held by the Institut Pasteur, Paris France.

3. The cell line of claim 1, further
   (c) wherein the cells of the cell line comprise an expression vector comprising a polynucleotide coding for a polypeptide for treating primary or secondary ophthamological or neurological disorders; and
   (d) wherein the cells of the cell line can integrate non-tumorigenically into the retina of the mammalian host to produce the polypeptide in the eye.

4. A method of producing a polypeptide to treat primary or secondary ophthamological or neurological disorders, comprising incubating cells of the cell line of claim 3 in a biological compatible medium such that the cell line produce the polypeptide.

5. The method of claim 4, wherein the cells of cell line is implanted in an eye of a mammalian host in need thereof.

6. The method of claim 5, wherein the cells of cell line is implanted in the subretinal space of the mammalian host.

7. The cell line of claim 1, wherein the cells of the cell line further comprise a selection gene.

8. The cell line of claim 1, wherein the polynucleotide comprising the heat sensitive SV40 tsa58 T-antigen oncogene is located on an expression vector.

9. A method for treating primary or secondary ophthalmological or neurological disorders, comprising non-tumorigenically grafting cells of the rat retinal pigmentary epithelial cell line into the eye of a mammalian host,
   (a) wherein the cells of the cell line comprise a polynucleotide comprising a heat-sensitive oncogene; and
   (b) wherein the cells can non-tumorigenically integrate into the retina of the mammalian host.

10. The method of claim 9,
    (c) wherein the cells comprise an expression vector comprising a polynucleotide coding for a polypeptide to treat primary or secondary ophthamological or neurological disorders; and
    (d) wherein the cells can integrate non-tumorigenically into the retina of the mammalian host, to produce the polypeptide in the retina.

11. The method of claim 9, wherein the grafting of the cells is a surgical injection of the cells.

12. The method of claim 9, wherein the cells are surgically injected into the subretinal space of the mammalian host.

13. A method for making a non-tumorigenic rat retinal pigmentary epithelial cell line, comprising:
    (a) obtaining primary cultures of PVG rat retinal pigmentary epithelial cells;
    (b) immortalizing cells of the primary culture with a heat sensitive SV40 tsa58 T-antigen oncogene;
    (c) selecting the immortalized cells;
    (d) cloning a cell line by limiting dilution of the selected immortalized cells;
    (e) passaging a cloned cell line for at least 30 passages; and
    (f) selecting a passaged cell line that has a rat retinal pigmentary epithelial characteristic selected from the group consisting of pavement morphology, expression of RET-PE2, expression of cytokeratin, and combinations thereof.

* * * * *